US009002440B2

United States Patent
Berkow et al.

(10) Patent No.: US 9,002,440 B2
(45) Date of Patent: Apr. 7, 2015

(54) SYSTEM AND METHOD FOR CHARACTERIZING CIRCULATORY BLOOD FLOW

(71) Applicant: Intelomed, Inc., Wexford, PA (US)

(72) Inventors: Jan K. Berkow, Allison Park, PA (US); Anne M. Brumfield, Russellton, PA (US)

(73) Assignee: Intelomed, Inc., Wexford, PA (US)

( * ) Notice: Subject to any disclaimer, the term of this patent is extended or adjusted under 35 U.S.C. 154(b) by 0 days.

(21) Appl. No.: 13/839,534

(22) Filed: Mar. 15, 2013

(65) Prior Publication Data

US 2013/0267858 A1 Oct. 10, 2013

Related U.S. Application Data

(63) Continuation-in-part of application No. 13/178,966, filed on Jul. 8, 2011.

(60) Provisional application No. 61/428,367, filed on Dec. 30, 2010, provisional application No. 61/362,472, filed on Jul. 8, 2010.

(51) Int. Cl.
 *A61B 5/02* (2006.01)
 *A61B 5/00* (2006.01)
 (Continued)

(52) U.S. Cl.
 CPC ............ *A61B 5/7278* (2013.01); *A61B 5/02028* (2013.01); *A61B 5/02116* (2013.01);
 (Continued)

(58) Field of Classification Search
 USPC ........................................................ 600/526
 See application file for complete search history.

(56) References Cited

U.S. PATENT DOCUMENTS 5,370,122 A 12/1994 Kuning et al.
5,810,011 A 9/1998 Kuning
(Continued)

FOREIGN PATENT DOCUMENTS

EP 2392257 A2 7/2011
EP 1601287 B1 12/2012
(Continued)

OTHER PUBLICATIONS

Tao, et al. An Ultrawideband Radar Based Pulse Sensor for Arterial Stiffness Measurement (2007).*
(Continued)

*Primary Examiner* — Michael Kahelin
*Assistant Examiner* — Mitchell E Alter
(74) *Attorney, Agent, or Firm* — Pepper Hamilton LLP

(57) ABSTRACT

A computer-implemented method for characterizing circulatory blood volume and autoregulatory compensatory mechanisms to maintain circulatory blood volume is disclosed. A biological signal that emulates the arterial pulse wave is collected from a sensor. Three derived parameters are extrapolated from the biological signal. The first parameter, circulatory stress, reflects of the changes of the heart rate frequency. The second, circulatory blood volume, reflects the changes in the frequency strength of the heart rate frequency. The third, Pulse Volume Alteration (PVA) Index is a ratio of the sum of the strengths of the heart rate frequency harmonics to the strength of the heart rate frequency of the unprocessed biological signal. Each parameter is compared to a threshold value and assessed to determine an adequacy of circulatory blood volume and an appropriateness of the autoregulatory mechanisms used to maintain circulatory blood volume adequacy.

15 Claims, 27 Drawing Sheets

(51) Int. Cl.
*A61B 5/021* (2006.01)
*A61B 5/026* (2006.01)
*A61B 5/024* (2006.01)
*A61B 5/1455* (2006.01)

(52) U.S. Cl.
CPC ........... *A61B5/0261* (2013.01); *A61B 5/02416* (2013.01); *A61B 5/7225* (2013.01); *A61B 5/726* (2013.01); *A61B 5/1455* (2013.01); *A61B 5/7257* (2013.01); *A61B 5/0002* (2013.01)

(56) References Cited

U.S. PATENT DOCUMENTS

| | | | |
|---|---|---|---|
| 5,830,131 | A | 11/1998 | Caro et al. |
| 5,865,756 | A | 2/1999 | Peel, III |
| 5,900,433 | A | 5/1999 | Igo et al. |
| 6,112,115 | A | 8/2000 | Feldman et al. |
| 6,126,595 | A * | 10/2000 | Amano et al. ............... 600/300 |
| 6,217,522 | B1 | 4/2001 | Shoshan |
| 6,270,461 | B1 | 8/2001 | Chio |
| 6,287,608 | B1 | 9/2001 | Levin et al. |
| 6,315,735 | B1 | 11/2001 | Joeken et al. |
| 6,334,849 | B1 | 1/2002 | Sunagawa |
| 6,339,716 | B1 | 1/2002 | Sawada et al. |
| 6,371,922 | B1 | 4/2002 | Baumann et al. |
| 6,485,431 | B1 | 11/2002 | Campbell |
| 6,575,912 | B1 | 6/2003 | Turcott |
| 6,719,705 | B2 | 4/2004 | Mills |
| 6,776,764 | B2 | 8/2004 | Pinsky |
| 6,858,006 | B2 | 2/2005 | MacCarter et al. |
| 7,044,918 | B2 | 5/2006 | Diab |
| 7,285,090 | B2 | 10/2007 | Stivoric et al. |
| 7,324,848 | B1 | 1/2008 | Turcott |
| 7,328,053 | B1 | 2/2008 | Diab et al. |
| 7,330,750 | B2 | 2/2008 | Erkkila et al. |
| 7,678,057 | B2 | 3/2010 | Berkow et al. |
| 7,794,406 | B2 | 9/2010 | Reisfeld et al. |
| 2001/0049476 | A1 | 12/2001 | Forstner |
| 2002/0045806 | A1 * | 4/2002 | Baker et al. ............... 600/309 |
| 2004/0039273 | A1 * | 2/2004 | Terry ............... 600/322 |
| 2005/0197675 | A1 | 9/2005 | David et al. |
| 2006/0293384 | A1 | 12/2006 | Whewell |
| 2007/0032732 | A1 * | 2/2007 | Shelley et al. ............... 600/504 |
| 2007/0088222 | A1 | 4/2007 | Berkow et al. |
| 2007/0123797 | A1 | 5/2007 | Kitajima et al. |
| 2007/0255146 | A1 | 11/2007 | Andrews et al. |
| 2008/0167564 | A1 * | 7/2008 | Hete et al. ............... 600/508 |
| 2008/0228090 | A1 | 9/2008 | Wariar et al. |
| 2008/0255471 | A1 | 10/2008 | Naghavi et al. |
| 2008/0269625 | A1 * | 10/2008 | Halperin et al. ............... 600/508 |
| 2010/0081947 | A1 | 4/2010 | Suzuki |
| 2011/0245691 | A1 | 10/2011 | Silber |
| 2013/0080489 | A1 | 3/2013 | Ochs et al. |

FOREIGN PATENT DOCUMENTS

| | | |
|---|---|---|
| WO | WO 03/077854 | 9/2003 |
| WO | WO 2004/084720 | 10/2004 |
| WO | WO 2005/107584 | 11/2005 |

OTHER PUBLICATIONS

Feissel, et al., Respiratory Variation of Plethysmography Signal with a Pulse Oximeter: New Predictive Parameters of Fluid Responsiveness?, *Proceedings of the American Thoracic Society* (Apr. 2006), 3:A295.

Kim, et al., Can Cardiac Contractility be Estimated by an Inspiratory Hold Maneuver?, *Proceedings of the American Thoracic Society* (Apr. 2006), 3:A296.

Kim, et al., Determinates of Arterial Pulse Pressure and Stroke Volume Variation during Positive-Pressure Ventilation, *Proceedings of the American Thoracic Society* (Apr. 2006), 3:A297.

Lamia, et al., Brachial Pulse Pressure is Related to Total Arterial Compliance and Stroke Volume in ICU Patients: An Arterial Tonometric Study, *Proceedings of the American Thoracic Society* (Apr. 2006), 3:A296.

Monnet, et al., Measuring Aortic Diameter is Essential for Assessing Fluid Challenge by Esophageal Doppler, *Proceedings of the American Thoracic Society* (Apr. 2006), 3:A296.

Ridel, et al., Prediction of Fluid Responsiveness in Spontaneously Breathing Patients: Response to Passive Leg Raising Measured by Pulse Contour Cardiac Output, *Proceedings of the American Thoracic Society* (Apr. 2006), 3:A295.

Zamanian, et al., Assessment of Cardiac Function and Ventilatory Efficiency by Noninvasive CO2 Monitoring during Reduction of Ventilatory Support in Patients with CHF, *Proceedings of the American Thoracic Society* (Apr. 2006), 3:A297.

International Search Report dated Nov. 4, 2014 for related International Application No. PCT/US2014/040890.

* cited by examiner

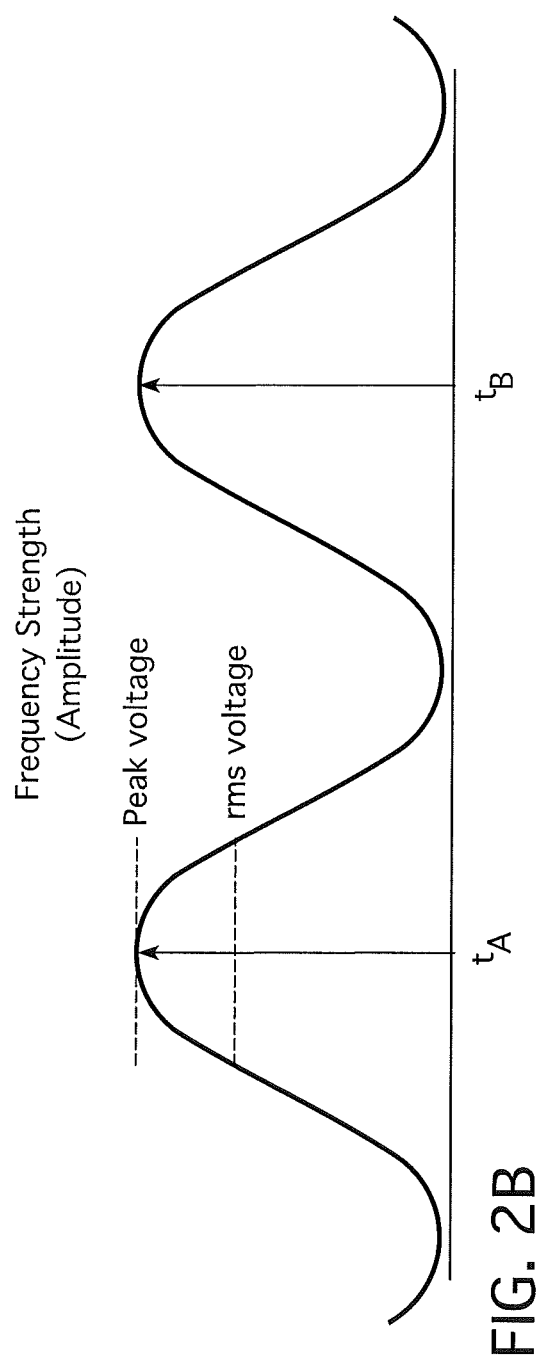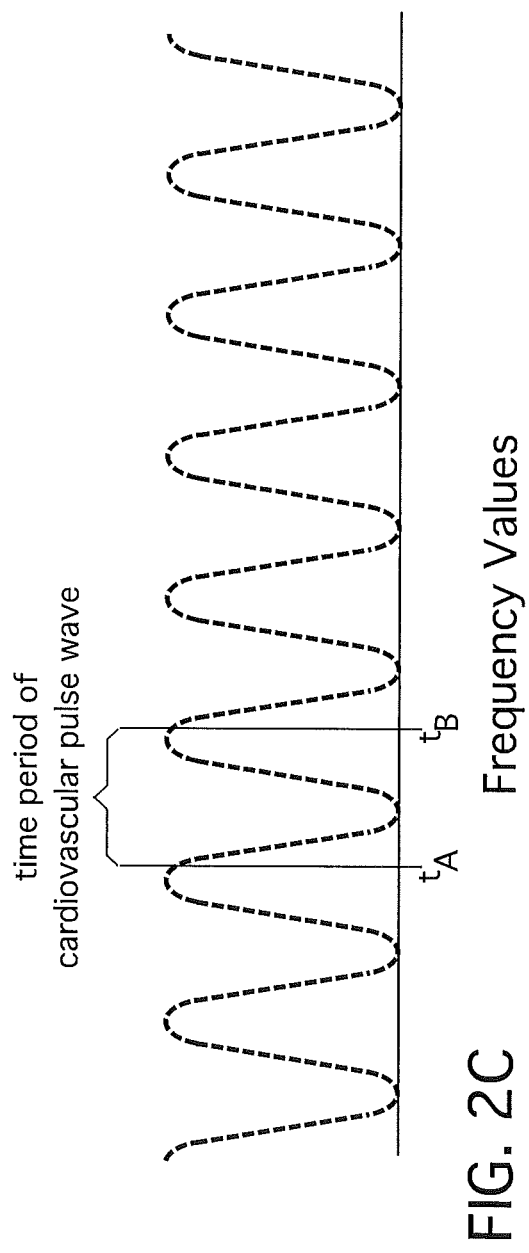

SYSTEM AND METHOD FOR CHARACTERIZING CIRCULATORY BLOOD FLOW

CROSS-REFERENCE TO RELATED APPLICATIONS

The present application claims priority to U.S. application Ser. No. 13/178,966, filed Jul. 8, 2011, which claims priority to U.S. Provisional Patent Application No. 61/362,472, filed on Jul. 8, 2010, and U.S. Provisional Patent Application No. 61/428,367, filed on Dec. 30, 2010.

BACKGROUND

Circulatory blood flow delivers oxygen and nutrients to tissues and organs and removes toxins and wastes therefrom. Such delivery and removal is essential to maintaining cellular function and tissue and organ health. Broadly defined, stress is the aggregate impact of physical, cognitive, pathological, and environmental factors to which an organism must adapt in order to remain in a physiologically homeostatic state. Adequate circulatory blood volume must be maintained under varying forms and degrees of stress, or else homeostasis and adequacy of oxygenated blood flow delivery is compromised. Accordingly, in the healthy state, the autonomic nervous system continuously adjusts circulatory blood volume in order to meet these constantly changing demands. In situations where the ability to adjust circulatory blood volume is inadequate, the delivery of oxygen and nutrients to tissues and organs and the removal of toxins and wastes therefrom is inadequate to meet the cellular demands and, as a result, overall physiological function is compromised.

Systems and methods for evaluating the condition of the autoregulatory components of the cardiovascular system are known in the art. Unfortunately, while these systems and methods are good predictors of the overall cardiovascular condition resulting from long-term pathological and age-related structural changes, they cannot characterize the functional adequacy of circulatory blood volume in the short-term. As such, in the face of stress, any resultant deficiencies in supplying the demands of the tissue and organs is often not detected until physiological function is so compromised that tissue and organ dysfunction become symptomatic and sustainability is at risk. Furthermore, while levels of certain metabolites are indicative of inadequate circulatory blood volume, such metabolites are only present after prolonged inadequate circulatory blood volume has occurred and therefore cannot characterize the functional adequacy of circulatory blood volume in the pre-symptomatic stages to avoid a compromised physiological state that may be irreversible. Thus, there is a need for real-time systems and methods that characterize the adequacy of circulatory blood volume over contiguous, finite time intervals in order that circulatory blood volume may be assessed and any deficiencies in supply may be detected and treated before the patient's sustainability is at risk.

SUMMARY

In an embodiment, a computer-implemented method for characterizing circulatory blood volume is disclosed. The method has the steps of acquiring a biological signal from a sensor, wherein the biological signal emulates the arterial pulse wave, conditioning the biological signal to create a conditioned signal, processing the conditioned signal, and calculating a derived parameter from the conditioned signal. In embodiments, three derived parameters are extrapolated from the biological signal, circulatory stress, which reflects changes in a harmonic or the fundamental frequency of heart rate, circulatory blood volume, which reflects changes in the frequency strength (or amplitude) of the unprocessed biological signal, and the Pulse Volume Alteration (PVA) Index, which is a ratio of the sum of the strength of the heart rate harmonic frequencies (non-cardiac contributions) within the arterial pulse wave to the strength of the heart rate frequency (cardiac contribution) which is equivalent to the acoustical calculation referred to as the Total Harmonic Distortion. Each derived parameter is compared to a threshold value. The heart rate and circulatory blood volume threshold comparisons are assessed to determine an adequacy of circulatory blood volume. The PVA Index is assessed to measure the stiffness in the underlying arterial structure caused by either autonomic nervous system driven vascular changes or from fluid transfer into (volume loading) or out of the arterial tree (volume loss or exanguination). In embodiments, changes in the circulatory stress and circulatory blood volume are extrapolated from changes in the frequency and frequency strength, respectively, of the arterial pulse wave in order to characterize changes in circulatory blood volume over contiguous, finite time intervals. In embodiments, the assessment of circulatory blood volume is used to manage a patient's cardiovascular autoregulatory function or the adequacy of transfer of fluids to and from the circulatory system, with the ultimate goal of achieving a circulatory blood volume that adequately supplies the demands of the patient's tissues and organs. In embodiments, the PVA Index is a measure of arterial structural stiffness and is used to assess the degree of fluid loading or deficiency or the degree to which the sympathetic response has been activated, which is the primary autoregulatory mechanism used to defend against circulatory volume changes.

In another embodiment, a system for characterizing circulatory blood volume is disclosed. The system has a processor that includes at least one module configured to process the biological signal and to calculate the derived parameters of circulatory stress and circulatory blood volume, and PVA Index therefrom. In embodiments, the processor includes a signal conditioning module configured to receive the biological signal from the sensor and to condition the biological signal. The processor also includes a signal processing module that is configured to process the biological signal to calculate the derived parameters. An analysis module is configured to assess the adequacy of a patient's cardiovascular autoregulatory function, the adequacy of transfer of fluids to and from the circulatory system, or the adequacy of the compensatory contributions by the vasculature with the ultimate goal of achieving a circulatory blood volume that meets the demands of the patient's tissues and organs.

In another embodiment, a computer-implemented apparatus for assessing circulatory blood volume is disclosed. The apparatus has means for acquiring the biological signal, means for conditioning the biological signal, means for processing the conditioned biological signal, and means for calculating the derived parameterscirculatory stress, circulatory blood flow, and the PVA Index from the conditioned signal. The apparatus further includes means for comparing each derived parameter to a threshold value and is used to assess the adequacy of circulatory blood volume and the effectiveness of the compensatory mechanisms in so doing. In embodiments, changes in the circulatory stress and circulatory blood volume are extrapolated from changes in the frequency and frequency strength, respectively, of the arterial pulse wave in order to assess the adequacy of the changes in circulatory blood volume over contiguous, finite time intervals. In embodiments, the PVA Index is extrapolated from the Total Harmonic Distortion calculation extrapolated from the arterial pulse wave and is used to characterize changes in the vasculature compliance to assess the degree to which the sympathetic response has been activated. In embodiments, the assessment of circulatory blood volume is used to manage a patient's cardiovascular autoregulatory function or the adequacy of transfer of fluids to and from the circulatory system, with the ultimate goal of achieving a circulatory blood volume that adequately supplies the demands of the patient's tissues and organs.

In another embodiment, a non-transitory computer-readable medium having stored therein instructions which, when executed by a processor, causes the processor to acquire the biological signal from a sensor, wherein the biological signal emulates the arterial pulse wave, conditions the biological signal to create a conditioned signal, processes the conditioned signal, and calculates the derived parameters, circulatory stress, circulatory blood volume, and the PVA Index from the conditioned signaldistortion. The computer-readable medium also has instructions stored therein to compare each derived parameter to a threshold value and to assess each derived parameter to determine an adequacy of circulatory blood volume and the effectiveness of the compensatory mechanisms. In embodiments, changes in the frequency (circulatory stress), frequency strength (circulatory blood flow), and the Total Harmonic Distortion (PVA Index) are extrapolated from changes in the frequency, changes in frequency strength, and a ratio of frequency strengths respectively extrapolated from the arterial pulse wave in order to assess the adequacy of an anesthestic during surgical care and its impact on adequacy of circulatory blood volume over contiguous, finite time intervals. In embodiments, changes in the frequency (circulatory stress), frequency strength (circulatory blood volume), and Total Harmonic Distortion measures (PVA Index) are extrapolated from changes in the frequency, changes in frequency strength, and changes in the ratio of frequency strengths respectively, of the arterial pulse wave in order to assess the appropriateness of antihypertensive medications and their impact on the effectiveness of the autoregulatory function in maintaining adequate circulatory blood volume over contiguous, finite time intervals. In embodiments, the assessment of circulatory blood volume is used to manage a patient's cardiovascular autoregulatory function or the adequacy of transfer of fluids to and from the circulatory system, with the ultimate goal of achieving a circulatory blood volume that adequately supplies the demands of the patient's tissues and organs.

Those and other details, objects, and advantages of the present invention will be become better understood or apparent from the following description and drawings showing embodiments thereof.

BRIEF DESCRIPTION OF THE DRAWINGS

Various embodiments of the present invention are described herein by way of example in conjunction with the following figures, wherein.

DETAILED DESCRIPTION

As used herein, "arterial pulse wave" means the pressure wave that results from the ejection of blood from the left ventricle of the heart during systole and the aggregate of vascular effects on the pressure wave.

A system and method is described herein to extract morphology-related features of the arterial pulse wave using frequency domain-based techniques that are captured in response to a stress condition. One or more features are then used to assess the short-term functional adequacy of circulatory blood volume to adapt to the stress condition. The inventive system and method can be used to assess the aggregate of cardiovascular adaptive mechanisms that contribute to maintaining adequate circulatory blood volume referred to as the cardiovascular autoregulatory system. The inventive system and method can also be used to assess specific autoregulatory components by isolating specific arterial pulse wave morphology features. Given that these frequency-based measures represent an aggregate of physiological effects, various embodiments may use ratios, summations, or other mathematic manipulations of changing frequencies, frequency strengths (amplitude), and/or other features resulting from the power spectrum analysis in order to isolate a cardiovascular autoregulatory component of interest. Other embodiments include ratios, summations, and mathematical formulae wherein weighted variables for elements resulting from either or both frequency and time domain analyses are combined.

Figure 1:
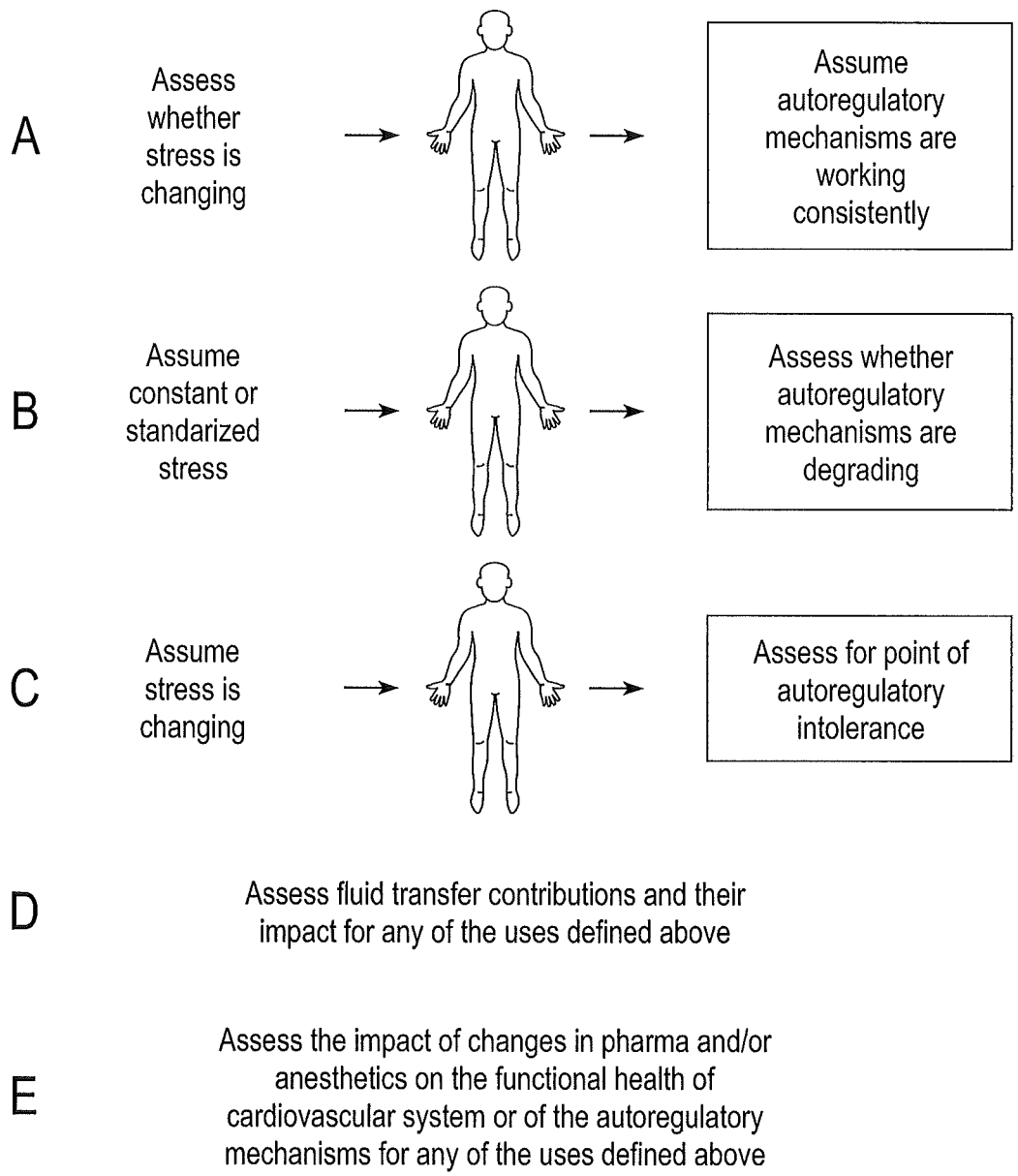
FIG. 1 illustrates embodiments of use of the inventive system and method.

The system may be used for various clinical applications, embodiments of which are illustrated in FIG. 1. In various embodiments, the system may be used to assess the appropriateness of the functional health of the cardiovascular autoregulatory mechanisms by employing a controlled stress condition and assessing the adequacy of the response. A standardized stress maneuver such as a sit-to-stand orthostatic test may be used for this purpose (FIG. 1A). In other embodiments, the system may be used to assess whether the functional health of the cardiovascular system is degrading, such as by assessing the response to a standardized stress test when performed repeatedly over a period of time. A trend indicating a decrease in autoregulatory function indicates, in a chronic heart failure patient, that the cardiac muscle is degrading and the patient is in a decompensating condition (FIG. 1B). In various other embodiments, the system may also be used to assess whether a patient has an intolerant circulatory volume condition, such as by using the system to monitor stability for an end-stage renal disease patient undergoing controlled fluid removal during a dialysis treatment performed over time (1C). In this instance, the system may be used to predict a hypotensive event arising from the induced hypovolemic state (i.e., resulting from fluid removal) (1D). In other embodiments, the system may be used to assess the effect of pharmaceuticals or anesthestics on the autoregulatory function (1E).

Figure 2A:
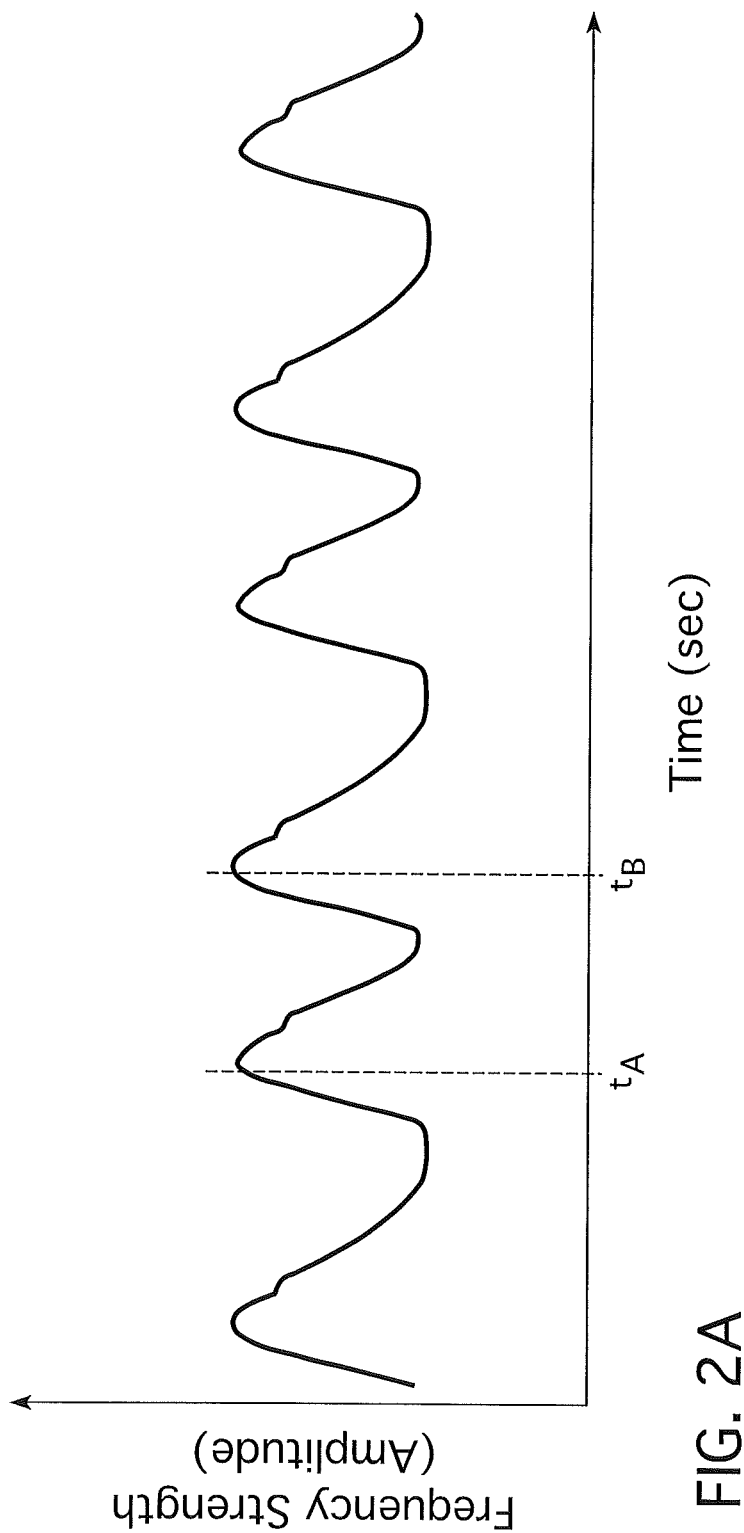
FIG. 2 illustrates an embodiment of the arterial pulse wave (A) and the corresponding frequency strength (amplitude) (B) and frequency (C).
Figure 4:
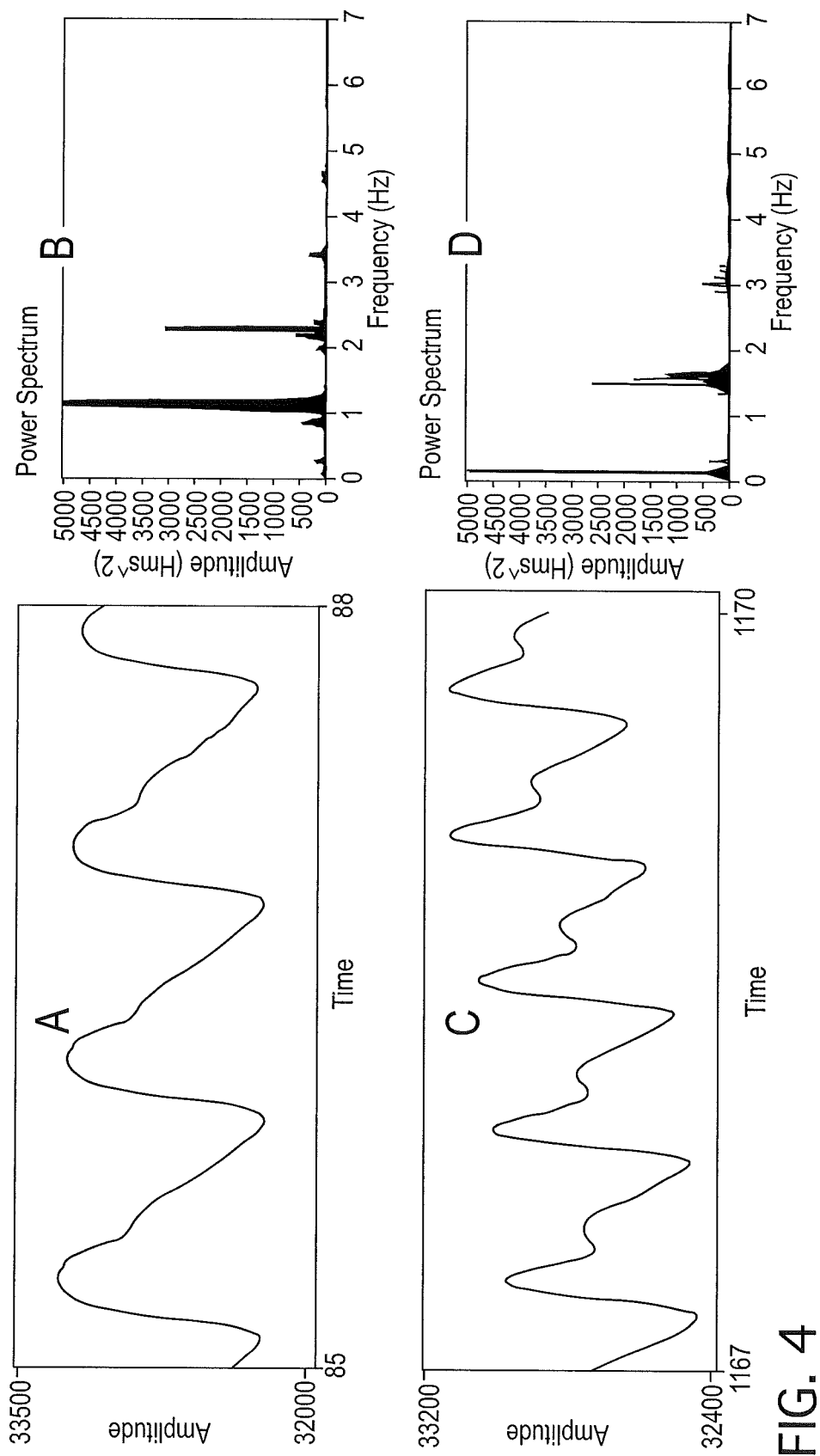
FIG. 4 illustrates embodiments of an arterial pulse waves acquired from a sensor placed on a healthy subject's forehead. Panel A illustrates the arterial pulse wave at rest and Panel B illustrates the power spectrum of the arterial pulse wave illustrated in Panel A. Panel C illustrates the arterial pulse wave during simulated blood loss created by placing the subject in a lower body negative pressure chamber and Panel D illustrates the power spectrum of the arterial pulse wave illustrated in Panel C.

Embodiments of the present invention utilize a biological signal that emulates the arterial pulse wave. The arterial pulse waveform morphology, an example of which is shown in FIG. 2A, represents a composite of frequencies of varying strengths. The system and method provide a more quantitative means by which to characterize the morphology changes that may otherwise be limited to a qualitative measure when capturing time-series based changes to the arterial pulse wave. The utility of the invention is illustrated in FIG. 4, which shows the arterial pulse wave in a patient at rest (Panel A) and the corresponding power spectrum (Panel B). During dialysis treatment, there is a change in the arterial pulse wave (Panel C) and a corresponding change in the power spectrum (Panel D) which represents the resulting changes from fluid removal during dialysis. In an embodiment, assessing specific arterial pulse frequency-based changes in response to an ongoing or created stress provides a method for assessing short-term cardiovascular functional changes and related cardiovascular functional conditions by evaluating the frequency changes associated with the heart rate, referred to herein as circulatory stress and depicted in FIG. 2B, and the frequency strength of the unprocessed biological signal, referred to as circulatory blood volume and depicted in FIG. 2C.

In various embodiments, use of frequency-based mathematical calculations such as summations or ratios are used to determine the degree to which a specific derived cardiovascular parameter contributes to the cardiovascular condition. The system and method are an alternative to more conventional systems and methods which measure arterial pulse wave frequency changes in the steady state to quantify long-term cardiovascular structural changes that result from aging or chronic pathological conditions.

In various embodiments, normalization of the derived parameter is needed to generalize measured changes to accommodate differences in cardiovascular efficiencies and for physiological properties related to the signal transducer employed. In various embodiments, when a photo-optic signal is employed, normalization is performed by capturing a baseline value for the derived parameters occurring during a steady state condition and providing measures in terms of percentage of change from this baseline value. In addition to normalizing for varying cardiovascular efficiencies, percentage of change enables normalization for changes in photo-optic signal attenuation due to varying levels of melanin in the skin.

Use of such a biological signal acquired from a non-invasive sensor presents fewer risks to the patient, in embodiments is less sensitive to motion and noise, and enables broad use, including use outside of a clinical setting, such as in the home, on an athletic field, etc. Use of changes for a specified frequency domain enable removal of undesirable physiological artifacts such as those from respiration or the nervous system and environmental artifacts such as from motion, noise, and electrical sources.

In various embodiments the systems and methods of the present invention extrapolate changes in two derived parameters, the frequency strength and frequency change of the biological signal over contiguous, finite time intervals, referred to herein as circulatory blood flow and circulatory stress, respectively, in order to characterize changes in circulatory blood volume and circulatory stress, respectively, over time. Averaging values in this way over contiguous time windows provides an additional filtering method for example, to reduce the effects of motion, noise, and the modulation effects of respiration on the circulatory volume (frequency strength) parameter.

Figure 3A:
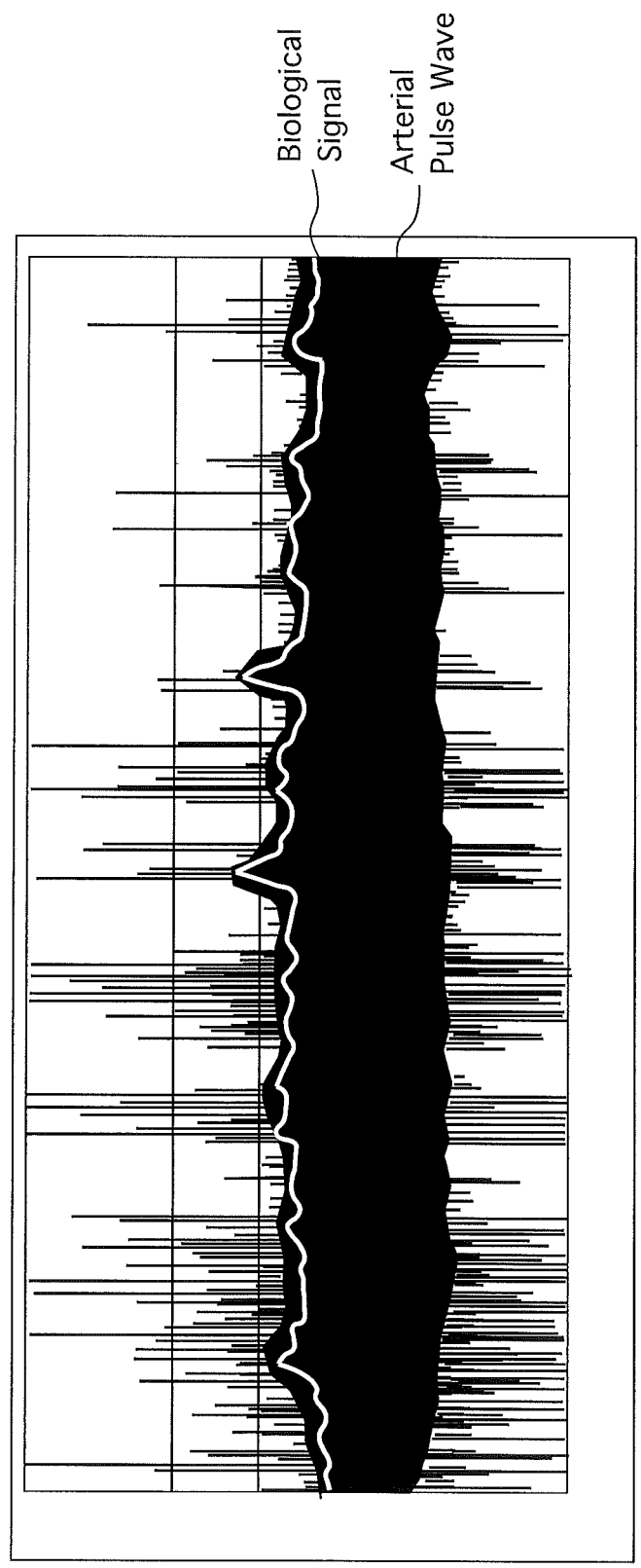
FIG. 3 illustrates (A) an embodiment of the biological signal super-imposed on the arterial pulse wave and (B) graphical depictions of the derived parameters circulatory stress (top), which reflects a harmonic of heart rate, and circulatory blood flow (middle), which reflects the amplitude of the unprocessed biological signal. An embodiment of the automated event monitoring system display is also illustrated (bottom). The top, middle, and bottom panels in (B) are vertically aligned in time. The biological signal and arterial pulse wave were recorded in a patient undergoing dialysis treatment.
Figure 3B:
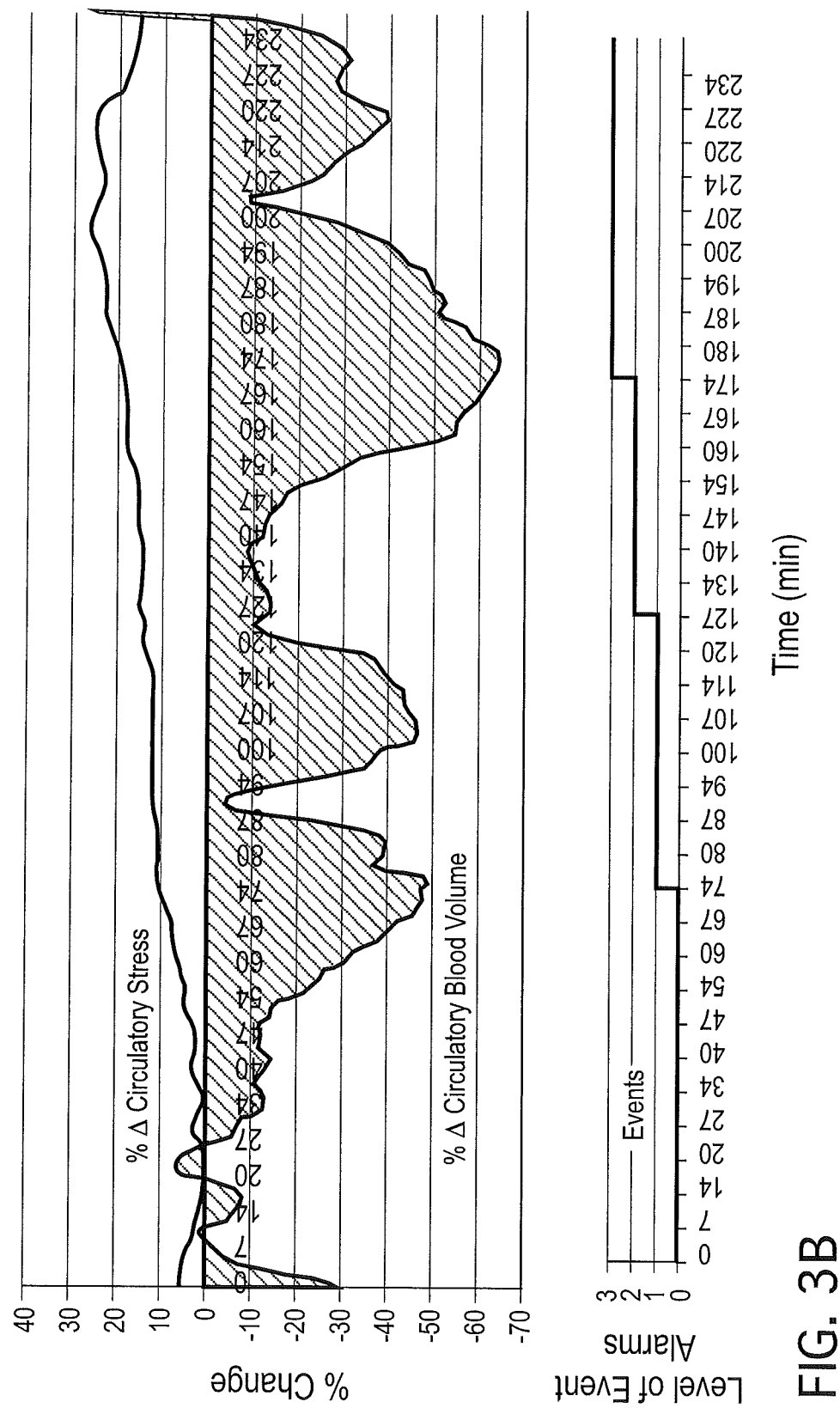

FIG. 3A illustrates an arterial pulse wave acquired from a photo-optic sensor placed on the forehead of an end-stage renal failure patient undergoing dialysis treatment. The derived parameter circulatory blood flow, which represents changes in the frequency strength of the heart rate frequency or any of the heart rate frequency harmonics, captured from the same patient using the system and method is shown superimposed on the arterial pulse wave, demonstrating that the acquired biological signal correlates with a filtered amplitude of the arterial pulse wave. FIG. 3B graphically depicts circulatory stress (top) and circulatory blood volume (middle) over time and are derived from the biological signal similar to FIG. 3A. This figure illustrates how two components derived from the arterial pulse wave, referred to herein as derived parameters, can be used to assess circulatory blood volume adequacy. One derived parameter, circulatory stress, is illustrated in the top panel and is a functional indicator of the current adequacy of the supply of circulatory blood volume to satisfy physiological demand. Another derived parameter, circulatory blood volume, is illustrated in the middle panel and indicates changes in the frequency strength of the unprocessed biological signal. In use, the derived parameters are calculated as a percentage change from a steady state baseline value in order to normalize for varying types of physiologies and photo-optic measurement differences, such as variations that result from different patient skin types. In FIG. 3B, the bottom panel illustrates an embodiment of the automated event monitoring system display which includes various levels of an alarm depending upon the percent change of one or both of the derived parameters (i.e., an event) that is activated when specific threshold values are met, indicative of either predictive or correlative cardiovascular volume insufficiency states. In effect, percent change in the derived parameters circulatory stress (top) and circulatory blood volume (middle) are used together to characterize the adequacy of circulatory blood volume. The circulatory stress in effect is used to calibrate circulatory blood volume to indicate the values that are either predictive or correlative for when cardiovascular volume insufficiency (e.g. hypovolemia) exists. The top, middle, and bottom panels in FIG. 3B are aligned vertically in time.

In various embodiments, the systems and methods may be used to assess the adequacy of circulatory blood volume. In embodiments, the assessment of adequacy of circulatory blood volume may be used to manage a patient's cardiovascular autoregulatory function or the adequacy of transfer of fluids to and from the circulatory system, each of which can impact the adequacy of circulatory blood volume, with the ultimate goal of achieving a circulatory blood volume that adequately supplies the demands of the patient's tissues and organs.

Figure 5:
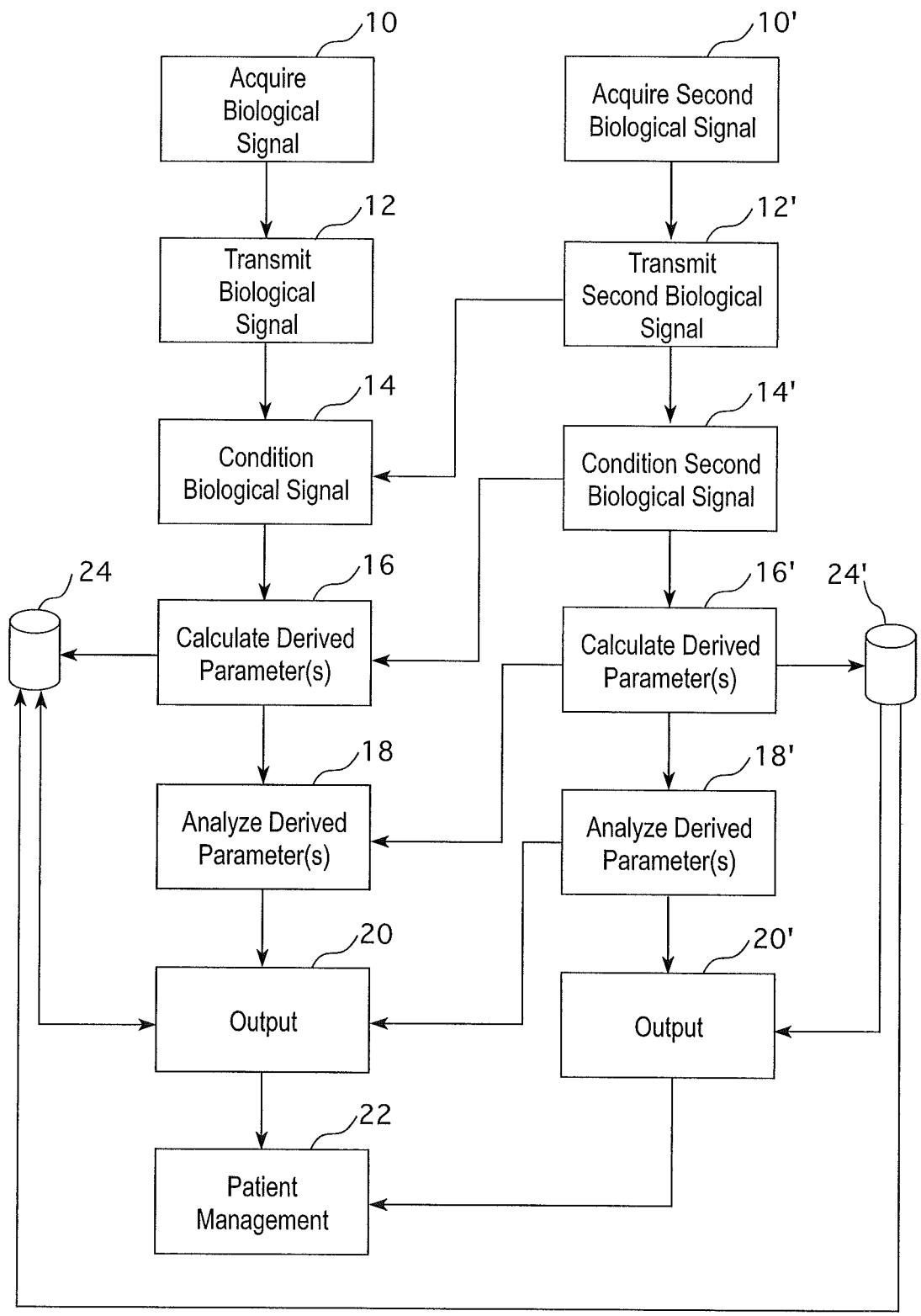
FIG. 5 illustrates a flowchart of various embodiments of a method for characterizing circulatory stress and circulatory blood volume.

FIG. 5 illustrates a flowchart of various embodiments of a method of acquiring derived parameters. In embodiments described herein, the derived parameters described are circulatory blood volume, circulatory stress, and the PVA Index. The skilled artisan will recognize that the system and method may be used to calculate any derived parameter that correlates with the arterial pulse wave. As described below, changes in the derived parameters over contiguous, finite time intervals may be used to characterize changes in circulatory blood volume, to assess adequacy of circulatory blood volume, and to provide a clinical management tool. As illustrated in FIG. 5, in embodiments, the present invention may be utilized in a method for managing a patient's health, such as the effectiveness of the cardiovascular autoregulatory function to compensate for changes in circulatory demand, the adequacy of circulatory blood volume, and the adequacy of the transfer of fluids to and from the circulatory system, the effect of pharmaceuticals such as hypertensive medications on the autoregulatory function, the effect of anesthetics on the autoregulatory function, the effects of environmental factors such as heat exhaustion on the autoregulatory function, the effect of cardiac functional health on the autoregulatory function, the effect of the vascular compensatory mechanisms on the autoregulatory function, the effect of adequate fluid resuscitiaton on the autoregulatory function, each of which can impact the adequacy of circulatory blood volume. The use of the present invention in methods of managing a patient's health have, in embodiments, the goal of achieving a circulatory blood volume that adequately supplies the demands of the patient's tissues and organs.

The steps illustrated in FIG. 5 may be performed in any order. At step 1, a biological signal is acquired from a sensor 10. As described below, the sensor 10 may be any invasive or non-invasive device that includes circuitry to acquire the biological signal. Examples of biological signals are provided in Table 2, below. In a preferred embodiment, the sensor 10 is a photo-optic sensor positioned on a patient's forehead. Such placement eliminates potential noise from respiration, movement, and the like and undesirable arterial transmission artifacts that occur when the sensor is placed at a distal location such as the finger.

At step 12, the acquired signal is transmitted from the sensor 10 to a processor via a wireline or wireless connection. In some embodiments, the acquired signal is stored to memory 70 at step 24, as described below.

At step 14, post-acquisition conditioning of the biological signal is performed. The post-acquisition conditioning may be specific to the sensor 10. In various embodiments, post-acquisition conditioning of the acquired biological signal includes any of a variety of steps implemented in circuitry, firmware, software, or any combination thereof to improve signal quality and sensitivity such as by normalizing variances, translating the signal to a form that is compatible with other elements of the system, etc. In embodiments, post-acquisition conditioning includes filtering the biological signal to remove noise, such as electrical noise, amplifying the biological signal, or converting the biological signal from an analog to a digital waveform. See FIG. 6, described below.

At step 16, the derived parameters, circulatory blood volume, circulatory stress, and the PVA Index are calculated and the circulatory blood volume and circulatory stress values normalized using the conditioned biological signal. In various embodiments, calculation of the derived parameters includes any of a variety of steps implemented in circuitry, firmware, software, or any combination thereof. See FIGS. 7-8, described below. Optionally, the derived parameters are stored in a memory 70 at step 24, described below.

Optionally, at step 18, the derived parameters are analyzed in order to assess the adequacy of circulatory blood volume. In various embodiments, analysis of the derived parameters includes any of a variety of steps implemented in circuitry, firmware, software, or any combination thereof. See FIG. 9, described below.

Optionally, at step 20, an output 60 such as that illustrated in FIG. 3B is generated to an output device that is in communication, via a wireline or a wireless connection, with the processor 90. Examples of output 60 include a graphical depiction of the derived parameters, an audio alarm that warns of an impending event, a communication to a caregiver or clinician that summarizes the assessment, etc. Optionally, output 60 is stored in a memory 70 at step 24, described below.

Optionally, at step 22, at least one of the derived parameters or the output 60 is used to manage a patient's cardiovascular autoregulatory function. In embodiments, management has the ultimate goal of achieving a circulatory blood volume that adequately supplies the demands of the patient's tissues and organs.

Optionally, at step 24, the derived parameters and/or output are stored in a memory 70 such as a database or a computer readable medium. In various embodiments, the derived parameters are stored in memory 70 together with a time stamp that identifies the time at which the derived parameter was calculated. In other embodiments, the derived parameters are stored in memory 70 together with a marker that identifies the stressor that was occurring at the point at which the derived parameter was calculated and may be used, for example, to create patterns of behavior to classify types of patients, as described below. For example, in a dialysis setting, derived parameters are stored in conjunction with a description that includes specifics of the stress applied, such as the volume of fluid removed. The data may be stored at step 24 locally or remotely. In various embodiments, the derived parameters and associated time stamp or stress measure are stored in conjunction with other patient-specific data, such as patient demographic parameters, patient co-morbidities, patient medications, and the like, in order to facilitate categorizing particular patterns of derived parameter responses to stress based upon these patient-specific data. In various embodiments, these patient classifications could be used to identify optimal treatment or intervention strategies for each patient classification. See FIG. 9, described below.

Referring again to FIG. 5, in various embodiments, a second sensor 10' is operated in parallel with the first sensor 10. At step 1', a second signal is acquired from the second sensor 10'. The second signal is processed in steps 12', 14', 16', and 18' as described above in steps 12, 14, 16, and 18. As illustrated in FIG. 5, the second signal may be processed by a second processor 90' that is collocated with the first processor 90 or the second signal may be processed by a second processor 90' that operates in parallel with the first processor 90. The second processor 90' includes at least one module 20', 30', 40' that processes and analyzes the second signal to generate an output 60.

Various embodiments of steps 14, 14', 16, 16', and 18, 18' are set forth in the flow charts illustrated in FIGS. 6-9. The embodiments illustrated in FIGS. 6-9 show the steps for calculating and normalizing the derived parameters, circulatory blood volume and circulatory stress, from a biological signal acquired from a photo-optic sensor and, in particular, a near infrared photo-optic device (frequency range of about 770-910 nm) such that density changes in both oxygenated and deoxygenated hemoglobin are acquired while light absorption by water is not acquired. Use of a photo-optic sensor is for illustration only and one skilled in the art will appreciate that any sensor that records a biological signal may be used for the inventive method and system.

Figure 17:
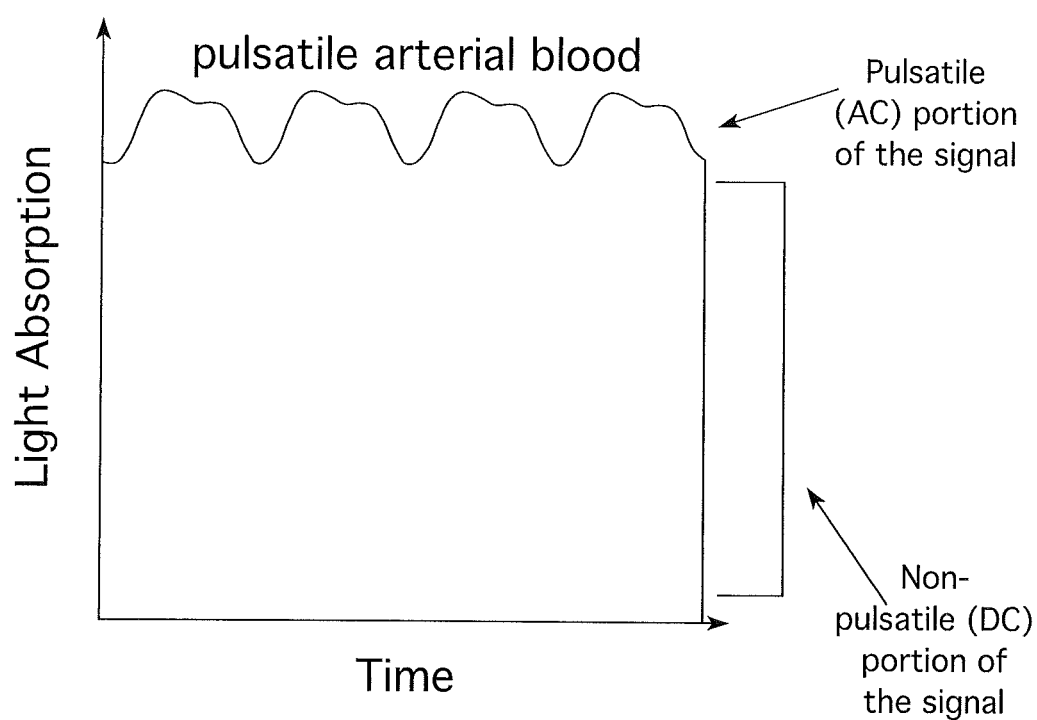
FIG. 17 illustrates the pulsatile and non-pulsatile portions of a photo-optic signal.

In an embodiment, the biological signal is a photo-optic signal that measures changes in absorption of light that result from changes in blood density that occurs as the arterial pulse wave is generated (see, e.g., FIGS. 2, 3). The resulting waveform acquired by the photo-optic device indicates the amount of light attenuated as light is transmitted through the blood. FIG. 17 illustrates all physiological components that attenuate the photo-optic signal as a result of absorption of the signal. The inventive system and method filter out all causes of light attenuation except the pulsatile portion of the signal because only the pulsatile portion indicates changes related to the arterial pulse wave. In various embodiment, the valley in the photo-optic signal occurs when the arterial pulse wave is at its peak (because light transmission decreases as the pulse wave is generated by systole and therefore the volume of circulating blood moving through the tissue increases) and the peak in the photo-optic signal occurs when the arterial pulse wave is at its valley (because light transmission increases as the pulse wave subsides and therefore the volume of circulating blood moving through the tissue decreases). In other embodiments, the biological signal could be a photo-optic signal that correlates to the changes in the strength of the reflection of the light resultant of changes in blood density in the optical path.

Figure 6:
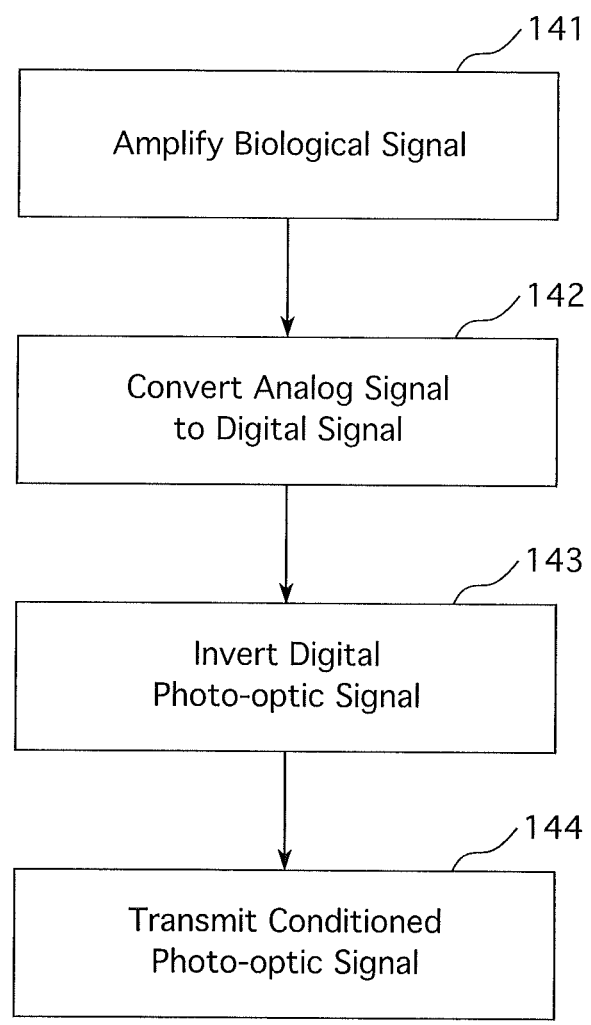
FIG. 6 illustrates a flowchart of various embodiments of the step of conditioning a biological signal.

The flow chart illustrated in FIG. 6 sets forth various embodiments of step 14. In embodiments, steps 141 through 144 are implemented in the signal conditioning module 30. The steps described herein may be performed in any order. In embodiments, the voltage that comes from the photo-optic device is small. Therefore, optionally at step 141, the biological or photo-optic signal is amplified. At step 142, the signal is converted from analog to digital. Optionally, at step 143, the signal is inverted so that the peak in the photo-optic signal occurs when the arterial pulse wave is at its peak and the valley in the photo-optic signal occurs when the arterial pulse wave is at its valley. At step 144, the converted, inverted (i.e., conditioned) signal is transmitted, via a wireline or wireless communication, to the signal processing module.

Figure 7:
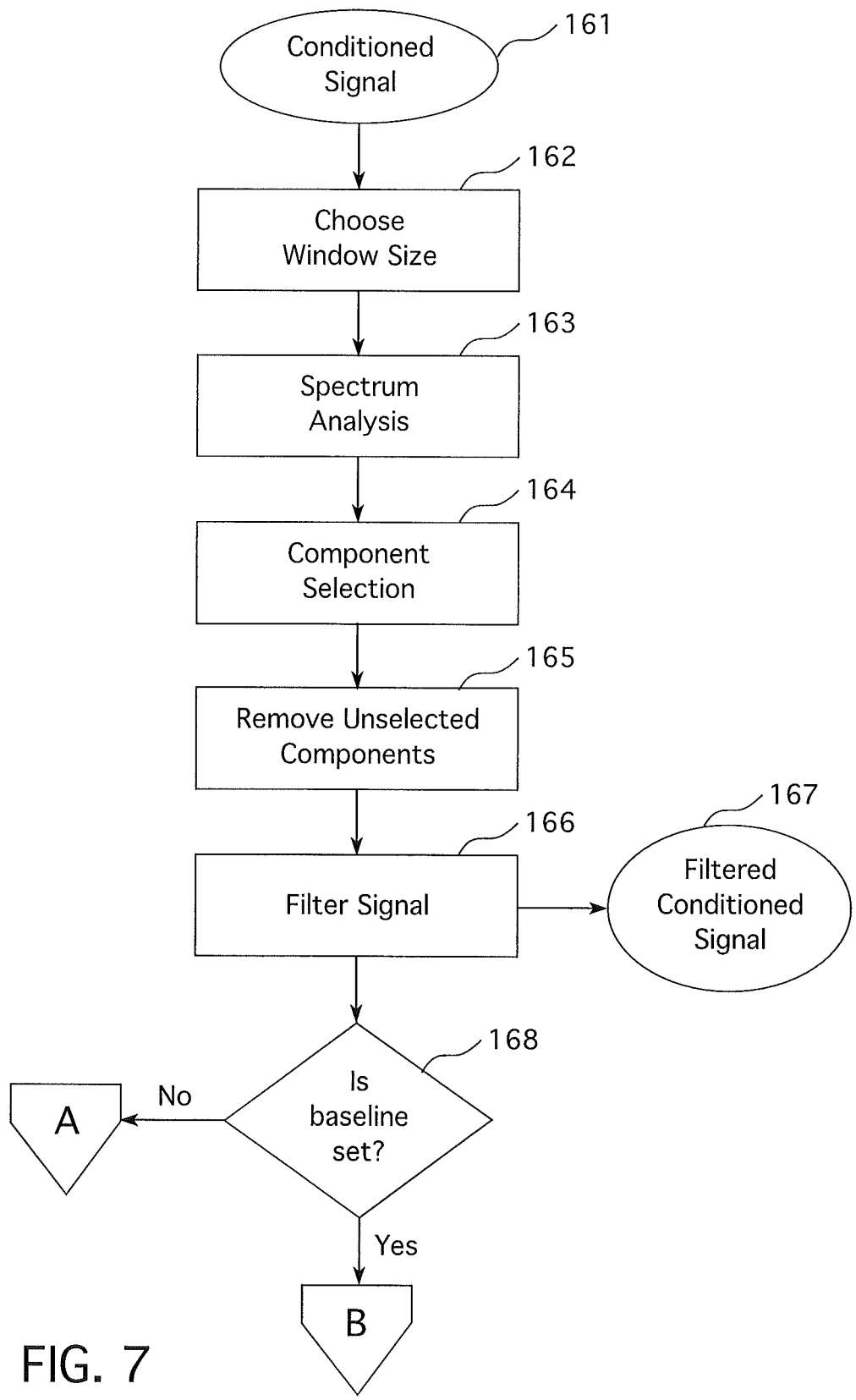
FIGS. 7-9 illustrate flowcharts of various embodiments of the steps of calculating and analyzing the conditioned biological signal.
Figure 8:
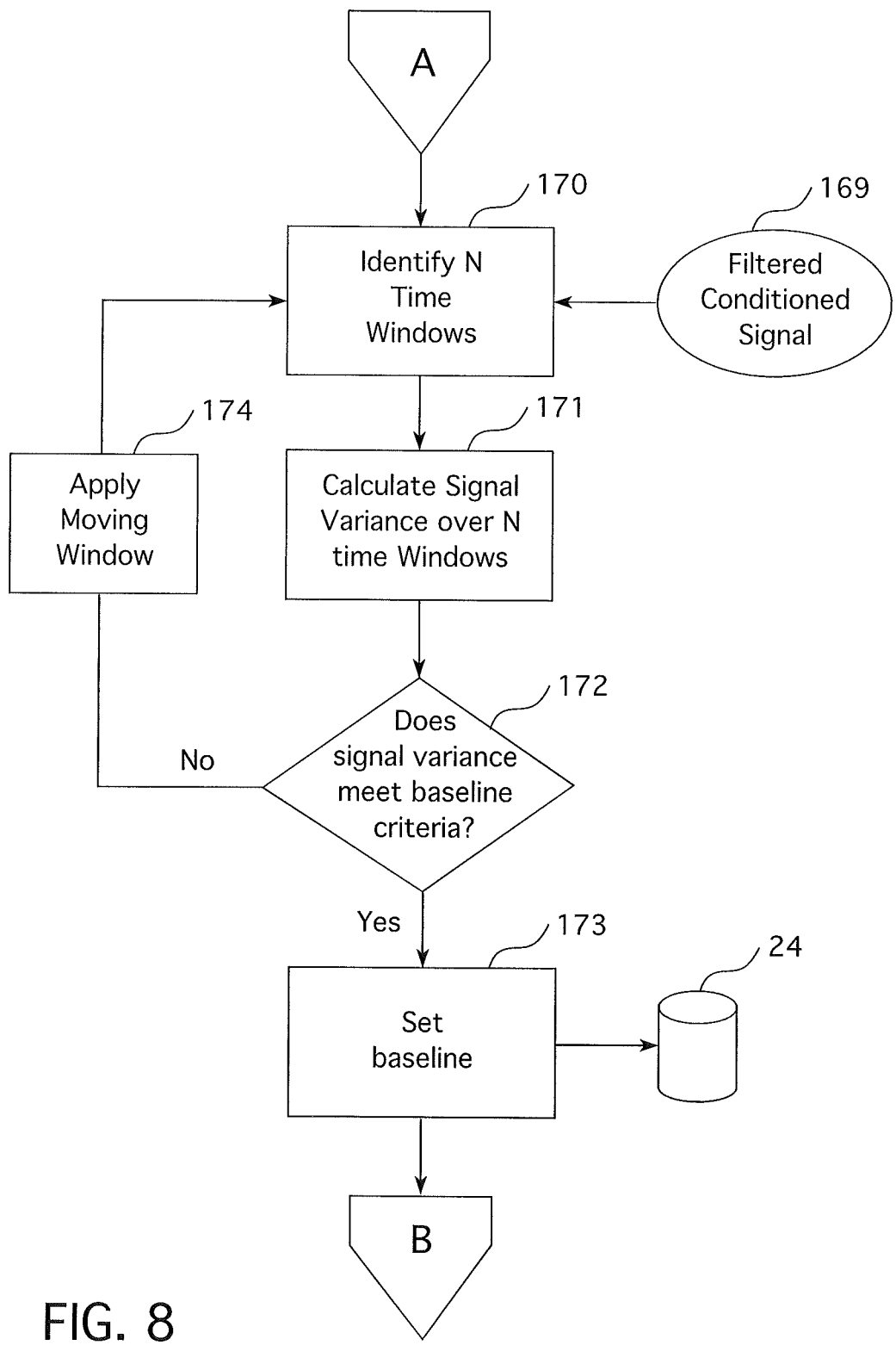
Figure 10:
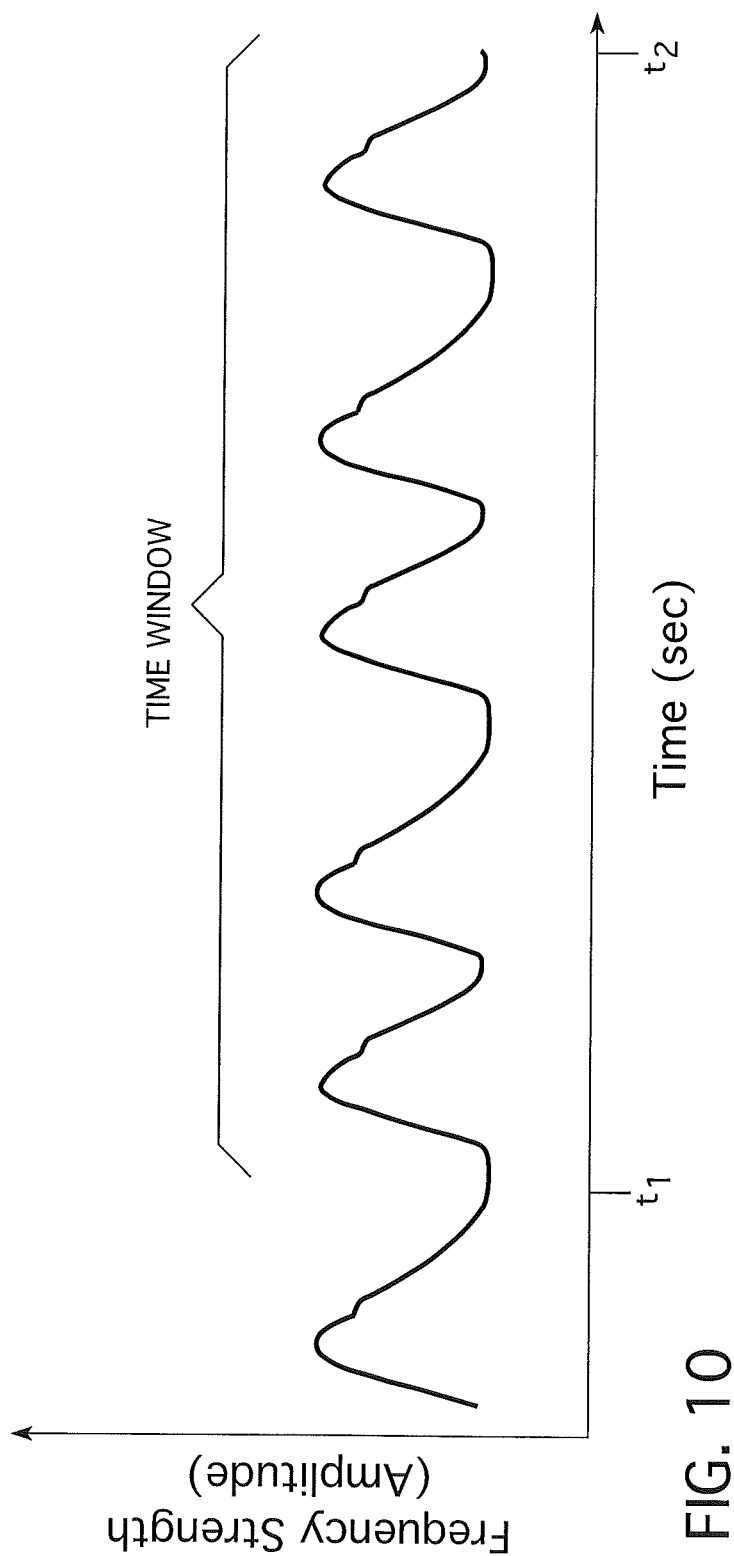
FIG. 10 illustrates a schematic of a biological signal broken down into a time window.

The flow charts illustrated in FIGS. 7-8 set forth various embodiments of step 16, shown in FIG. 5. The steps described herein may be performed in any order. Referring specifically to FIG. 7, in embodiments, steps 161 through 174 are implemented in the signal processing module 30. At step 161, the conditioned signal is received. At step 162, a window size N is used to break the conditioned signal into contiguous windows of data over discrete time intervals between time t1 and time t2, each referred to herein as a time window. Window size N is used at step 170, described below. An example of a time window is illustrated in FIG. 10. In various embodiments, the conditioned signal is broken into time windows each having a duration ranging from about 3 seconds to about 15 seconds, and in one embodiment each having a duration of about 10 seconds. Time windows of about 10 seconds each represent about ten cardiac cycles in a patient whose heart rate is about 60 beats per minute.

Figure 11B:
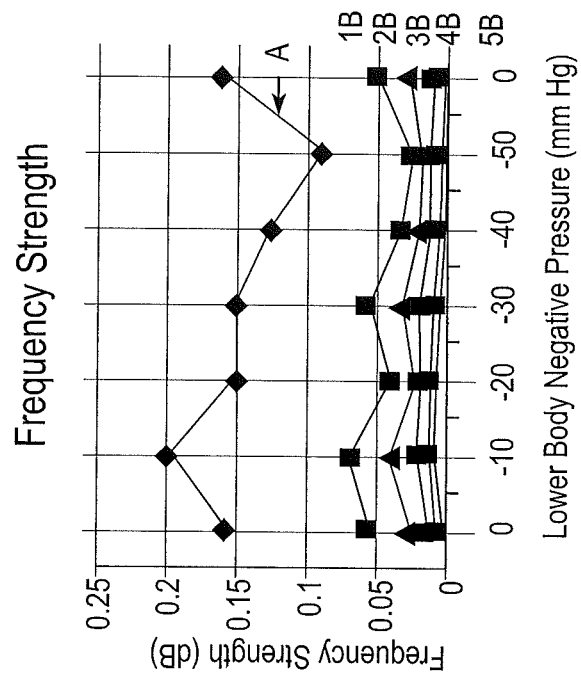
FIG. 11 illustrates the changes in frequency (A) and frequency strength (B) of the fundamental frequency for the biological signal and its component harmonics recorded in a patient exposed to a lower body negative pressure chamber.
Figure 11A:
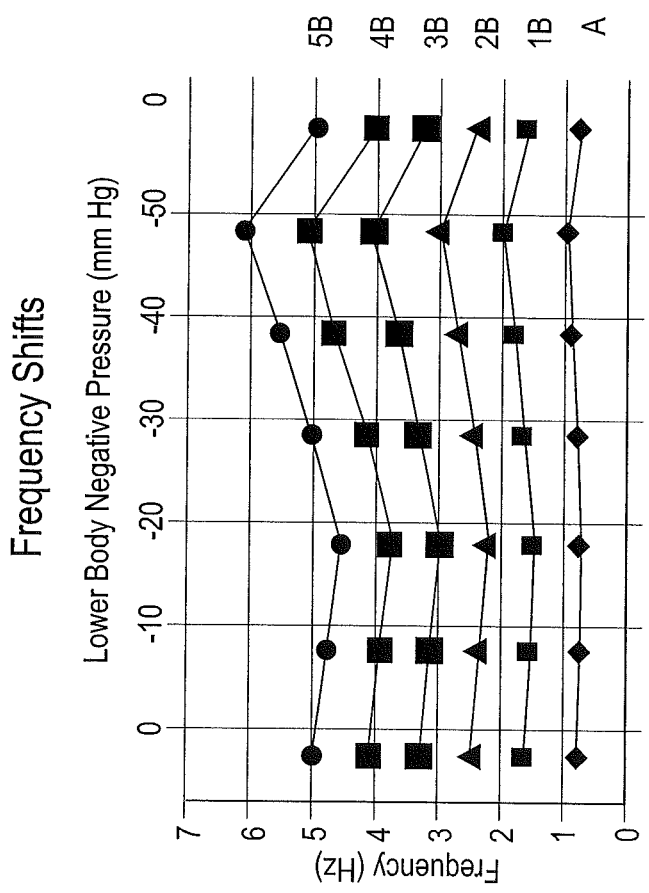

At step 163, for each time window, a spectrum analysis is performed on the conditioned signal that separates the conditioned signal into the fundamental and harmonic frequency bands. Step 163 may utilize any separation technique, algorithm, or the like known to those skilled in the art. In various embodiments, a Fast-Fourier Transform (FFT) algorithm is applied to the conditioned signal in each time window and separates the conditioned signal into the fundamental and harmonic frequency bands which comprise the conditioned signal. In various embodiments, a wavelet transformation is applied to the conditioned signal in each time window to separate the conditioned signal into the fundamental and harmonic frequency bands which comprise the conditioned signal. Examples of the fundamental and the first five harmonic frequency bands for the photo-optic signal are illustrated in FIG. 11. The fundamental signal A is depicted in solid line and the harmonics are identified as lines B1 through B5. The fundamental A or any of the harmonics B1 thru B5 may be used in embodiments for the calculation for circulatory stress or frequency shifts. Changes over time in frequencies and frequency strength over time are illustrated in FIGS. 11A and 11B, respectively. In the illustration shown in FIG. 11, the biological signal was acquired during changes in simulated blood loss created by decreases in pressure in a lower body negative pressure chamber.

At step 164, the component(s) of the signal are selected. In the embodiment shown in FIG. 11, the second harmonic (B2) is selected when the assessment is limited to the absolute value of the frequency because it may be more sensitive to centralized blood loss but is not limited by the condition of the patient's blood vessels (such as in a co-morbidity state). In contrast, the higher harmonics (i.e., B3-B5) are more sensitive to the condition of the patient's cardiovascular health. For example, an elderly patient with stiff blood vessels will have fewer harmonic frequencies than a younger subject with more supple blood vessels. In embodiments, selection of the most reliable harmonic is determined by patient population, resolution of the sensor used to acquire the biological signal, the stress employed, and other such variables. In embodiments, the system and method are used to determine the most reliable harmonic over various populations. In embodiments where the assessment is based upon percentage of change measures, either the fundamental frequency or any of the harmonics will produce the same quantitative results assuming the quality of each of the harmonics are the same.

At step 165, the selected harmonic(s), B2 and the fundamental signal in the embodiment shown, are maintained and the other harmonics are removed.

At step 166, a linear continuous-time filter is applied to smooth the selected harmonic B2 and the fundamental signal A and to generate a filtered, conditioned harmonic B2 and fundamental signal A at step 167. In various embodiments, a Butterworth Filter, implemented with a polynomial transfer function, is applied to the second harmonic and the fundamental photo-optic signal. Those skilled in the art will understand, however, that other filters may also be applied, including for example, Chebyshev, Bessel, Elliptical filters, custom low pass filter modules, and techniques using moving averagers.

At step 168, the method determines if a baseline has been set. If no baseline has been set, an embodiment of a baseline calculation is illustrated at steps 170 through 173, although those skilled in the art will understand that any method of identifying a baseline may be used herein. If a baseline has been set, then the derived parameters are calculated and analyzed as set forth in FIG. 9, described below.

Figure 23:
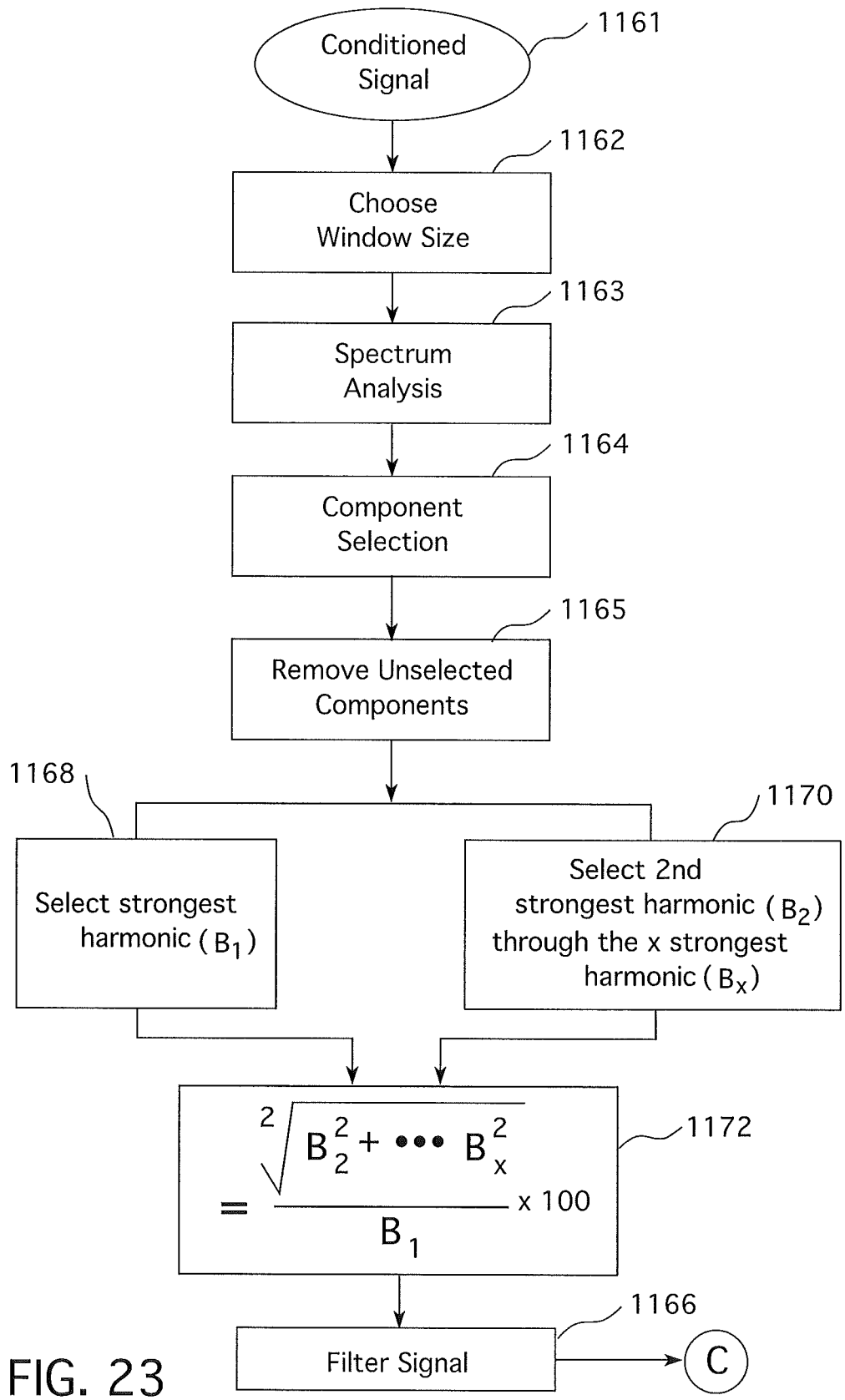
FIG. 23 illustrates a flowchart of an embodiment of a process for calculating and analyzing the conditioned biological signal.

The flow chart illustrated in FIG. 23 sets forth another embodiment of the calculation that is performed in FIG. 7. The steps described herein may be performed in any order. The embodiment illustrated in FIG. 23 employs a total harmonic distortion (THD) calculation to measure a third derived parameter referred to as the Pulse Volume Alterations (PVA) Index. The measure may be used to assess the degree of arterial compliance activation when placing the sensor on a large artery or degree of activation of arteriole constriction or tone when placing the sensor on a capillary bed. In other embodiments, this parameter may be used to indirectly assess the compliance related effects on a large artery resultant of changes to the effective circulatory volume resultant of vasoconstriction, the transfer of fluid into or out of the arterial tree, or the effects of anesthestetics or medications on the cardiovascular compensatory mechanisms.

The equation for calculating the PVA Index provides a ratio of the sum of the strengths of the heart rate related harmonic frequencies to the strength of the primary harmonic or fundamental frequency for the heart rate. When used to assess acoustical properties, the greater the numerator or summed harmonic strength, the greater the amount of acoustical distortion present. In the case of an arterial pulse wave, frequency decomposition reveals a primary harmonic or heart rate frequency and additional lesser strength harmonics that are integer multiples of the fundamental pulse wave frequency. It is the combination of these frequencies and their specific strengths that can be used to characterize the pulse wave morphology. De-activation of the sympathetic nervous system results in increases in the compliance of the arterial wall of the large arteries. Increases in arterial compliance results in the increase in the summed harmonics or integer multiple frequencies of the heart rate of the arterial pulse wave in proportion to the frequency strength of the fundamental heart rate frequency and a larger PVA Index. In the acoustical context, when a guitar string becomes more taut, the aggregate strength of the harmonic frequencies decreases in proportion the fundamental frequencies. Similarly, when the sympathetic nervous system is activated, the walls of the large arteries become less compliant, causing a decrease in the summed frequency strengths of the integer multiple frequencies of the heart rate or its harmonics.

An increase in the activation of the sympathetic nervous system results in an increase in the arterial tone or vascular constriction of the small arteries or arterioles. When the sensor is placed over a small arterial bed such as when placed on the finger, an increase in the arterial tone will result in a decrease in total harmonic distortion percentage. Alterations in the strength of the harmonics can also be attributed to long term structural changes that affect vascular stiffness in addition to short term autonomic nervous driven changes.

Referring specifically to FIG. 23, in embodiments, steps 1161 through 1172 are implemented in the signal processing module 30. At step 1161, the conditioned signal is received. At step 1162, a window size N is used to break the conditioned signal into contiguous windows of data over discrete time intervals between time t1 and time t2, each referred to herein as a time window. Window size N is used at step 170, described below. An example of a time window is illustrated in FIG. 10. In various embodiments, the conditioned signal is broken into time windows each having a duration ranging from about 3 seconds to about 15 seconds, and in one embodiment each having a duration of about 10 seconds. Time windows of about 10 seconds each represent about ten cardiac cycles in a patient whose heart rate is about 60 beats per minute.

At step 1163, for each time window, a spectrum analysis is performed on the conditioned signal that separates the conditioned signal into the fundamental and harmonic frequency bands. Step 1163 may utilize any separation technique, algorithm, or the like known to those skilled in the art. In various embodiments, a Fast-Fourier Transform (FFT) algorithm is applied to the conditioned signal in each time window and separates the conditioned signal into the fundamental and harmonic frequency bands which comprise the conditioned signal. In various embodiments, a wavelet transformation is applied to the conditioned signal in each time window to separate the conditioned signal into the fundamental and harmonic frequency bands which comprise the conditioned signal. Examples of the fundamental and the first five harmonic frequency bands for the photo-optic signal are illustrated in FIG. 11. The fundamental signal A is depicted in solid line and the harmonics are identified as lines B1 through B5. Changes over time in the shift of the frequencies and in the frequency strength over time are illustrated in FIGS. 11A and 11B, respectively. In the illustration shown in FIG. 11, the biological signal was acquired during changes in simulated blood loss created by decreases in pressure in a lower body negative pressure chamber.

At step 1164, the components (i.e., the harmonics) of the signal are selected using, for example, the process described herein in connection with FIG. 7. At step 1165, the selected harmonics are maintained and other harmonics are removed.

At step 1166, a linear continuous-time filter is applied to smooth the selected harmonics. In various embodiments, a Butterworth Filter, implemented with a polynomial transfer function, is applied to the harmonics and the fundamental photo-optic signal. Those skilled in the art will understand, however, that other filters may also be applied, including for example, Chebyshev, Bessel, Elliptical filters, custom low pass filter modules, and techniques using moving averages. At step 1168, the strongest harmonic (B1) is selected from the remaining harmonics for the denominator of the total harmonic distortion calculation of step 1172. At step 1170 the second strongest and all other harmonics in the remaining harmonics are selected for the numerator of the total harmonic distortion calculation of step 1172. At step 1172 the total harmonic distortion calculation is performed and the process advances to "C" on FIG. 9.

Referring now to FIG. 8, a filtered conditioned signal is continuously inputted at step 169 such that baseline is continuously recalculated as the filtered conditioned signal is received until baseline criteria are met. As shown, at step 170, a set of N time windows is selected for use in steps 171 through 173, described below. In an embodiment, the set of time windows N is 4 to 10 time windows. In a preferred embodiment, the set of time windows N is 6 time windows.

At step 171, the signal variance is calculated for each of the filtered conditioned signals received at step 169 in each window comprising the set of N time windows selected at step 170. In an embodiment, signal variance is the slope of the filtered conditioned signal received at step 169 in each of the N time windows. In another embodiment, signal variance is the percent change in the signal strength of the filtered conditioned signal received at step 169 in each of the N time windows, where strength is calculated according to the following Equation 1:

the root mean square (rms) of the peak voltage for one pulse wave in the photo-optic signal, where the root mean square is obtained by multiplying the peak voltage by 0.707.

In an example, in each of the N windows, the signal variance of the harmonic 2B is calculated as the slope of the harmonic frequency is calculated and the signal variance of the fundamental signal A is calculated as the percent change in the strength of the fundamental signal.

At step 172, the calculations from step 171 are compared to a pre-determined baseline criteria. If the calculations from step 171 meet the baseline criteria, then the baseline is set at step 173. In a preferred embodiment, if the slope of the harmonic frequency 2B over each of the N time windows is less than 0.1 and the percent change in the strength of the fundamental signal A is less than 10%, then the set of N time windows may be used as a baseline.

At step 24, the baseline is stored in a memory 70 such as a database or a computer readable medium.

If the calculations from step 171 do not meet the baseline criteria, then a moving window technique is applied to the signal(s) A and 2B at step 174 such that the set of time windows is moved forward by one time window and steps 170 through 172 are repeated until a baseline is set at step 173.

Figure 9:
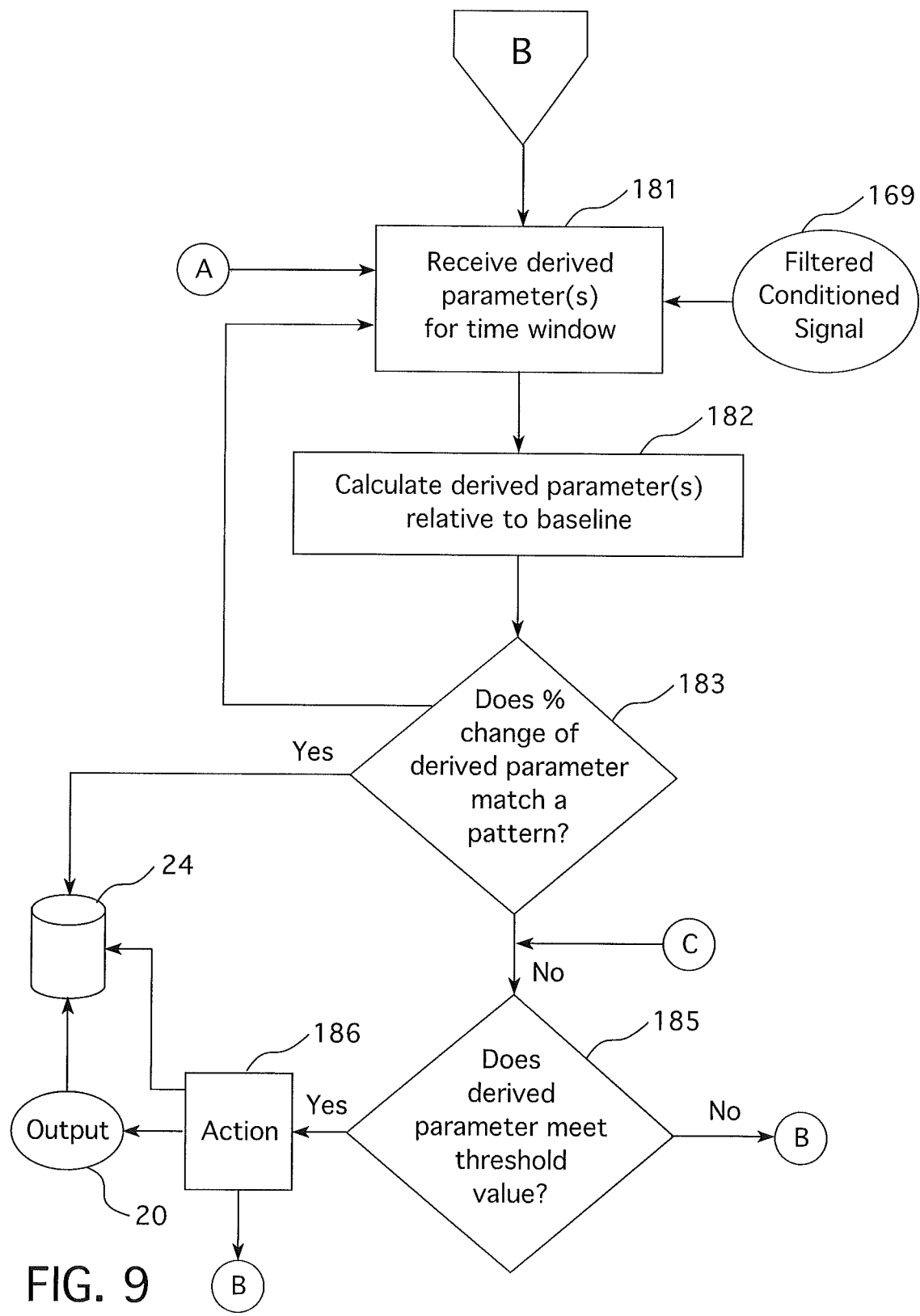

The flow chart illustrated in FIG. 9 sets forth various embodiments of step 18. In optional embodiments, steps 181 through 186 are implemented in the analysis module 40.

As illustrated in FIG. 9, in embodiments, the present invention may be utilized in a method for assessing the adequacy of circulatory blood volume. In the embodiment illustrated in FIG. 9, the analysis module 40 receives, via a wireline or a wireless connection, a filtered conditioned signal is continuously inputted at step 169 such that the filtered conditioned signal is continuously used to calculate the derived parameter(s) percent change from baseline as the filtered conditioned signal is received. At step 181, the filtered conditioned signal is received for analysis. At step 182, the derived parameter(s) percent change(s) from baseline are calculated. In an embodiment, the percent changes of the frequency and frequency strength parameters are calculated by dividing the respective derived parameter by the corresponding baseline for that derived parameter that was set in step 173. In an embodiment, a harmonic frequency value 2B is used as the derived parameter, circulatory stress, and Equation 1 is used to calculate the derived parameter, circulatory blood volume.

Optionally, at step 183, the pattern of at least one of the derived parameters over time is compared to a library of patterns of that derived parameter over time, where the library of patterns is stored in memory. The comparison at step 183 can be used to identify abnormal physiological conditions to which standard rules of autoregulatory volume adequacy cannot be applied, such as for example, where the patient has an arrhythmia, is taking medications that alter the autoregulatory function, or has other conditions that impact autoregulatory function. In embodiments, the patterns are stored in a look-up table. In embodiments, the library of patterns is a collection of previously recorded and stored derived parameters recorded from patients with known abnormal physiological conditions. In other embodiments, the library of patterns includes other external measurements such as blood pressure, oxygen saturation, core temperature, electrocardiology, skin temperature and the like. If at step 183, the derived parameter matches one of the patterns in the library of patterns, then the patient is classified into an outlier patient population and the threshold value, described at step 185 below, does not apply, and instructions are implemented to initiate an action at step 186. Optionally, an output 60 is generated at step 20. Optionally, the output and/or the action are stored in memory 70 at step 24.

If the patient is not in an outlier patient population, then at step 185, each derived parameter calculated at step 182 is compared to a threshold value, where the threshold value is a pre-determined value that represents a specific condition or level of circulatory blood volume adequacy. In embodiments, the threshold value is user-specified or has been clinically validated in a specific patient population. If the derived parameter meets the threshold value, then at step 186 instructions are implemented to initiate an action instructions are implemented to initiate an action. Optionally, an output 60 is generated at step 20. Optionally, the output and/or the action are stored in memory 70 at step 24.

Optionally, the filtered signal is continually received at step 169 and steps 181 through 186 and steps 20, 24 are repeated, as depicted in FIG. 9.

Examples of actions at step 186 include activation of an alarm that indicates a prediction that the patient is pre-symptomatic to an inadequate circulatory volume condition, or activation of an instruction to implement treatment to improve the patient's circulatory volume condition.

If the threshold is not met at step 185, then monitoring of the patient continues by repeating steps 169, 181 through 185. Even where the criteria are met, optionally, monitoring of the patient may continue by repeating steps 169, 181 through 185.

An example of a look-up table for the circulatory volume and circulatory stress parameters used at step 186 is shown in Table 1. As illustrated: (i) if a patient's circulatory stress value is 10% and the maintained circulatory blood flow is +/−10%, then the patient is at an "Alarm Level 1" and data are plotted on a trend graph and an alarm panel 1 light is lit; (ii) if a patient's circulatory stress value is 15% and the maintained circulatory blood volume is +/−10%, then the patient is at an "Alarm Level 2" and data are plotted on a trend graph and an alarm level 2 panel light is lit; (iii) if a patient's circulatory stress value is 20% and the maintained circulatory blood volume is +/−10%, then the patient is at an "Alarm Level 3" and data are plotted on a trend graph, an alarm level 3 panel light is lit, and an audio alarm is sounded; and (iv) if a patient's circulatory stress value is greater than or equal to 25% and the maintained circulatory blood volume is +/−10%, then the patient is at an "Alarm Level 4" and data are plotted on a trend graph, an alarm level 4 panel light is lit, and a high level alarm is sounded. In another embodiment, a look-up table would include a value of approximately 40% as normal range for the PVA Index for a healthy individual with ranges below 40% to indicate a sympathetically activated, increased effective circulatory blood volume, or fluid overload condition. Similarly, a value greater than 40% would indicate a parasympathetically activated, a decreased effective circulatory volume, or a circulatory volume insufficiency condition.

TABLE 1

| Event Alarms. | | | |
|---|---|---|---|
| | Circulatory Stress | Maintained Circulatory Blood Flow | Action |
| Alarm Level 1 | 10% | +/−10% | Plot data value on trend graph and light alarm level 1 panel light |
| Alarm Level 2 | 15% | +/−10% | Plot data value on trend graph and light alarm level 2 panel light |

TABLE 1-continued

Event Alarms.

| | Circulatory Stress | Maintained Circulatory Blood Flow | Action |
|---|---|---|---|
| Alarm Level 3 | 20% | +/−10% | Plot data value on trend graph and light alarm level 3 panel light, make light blink, and initiate low level audio alarm |
| Alarm Level 4 | 25% | +/−10% | Plot data value on trend graph and light alarm level 4 panel light, make light blink, and initiate high level audio alarm |

In another embodiment, step 183 is used to classify patients with similar physiological responses. A classification may indicate a group of patients with similar comorbidities and/or demographics that exhibit a similar physiological response to a form of stress. In this embodiment, step 186 is a look-up table is used to identify a standardized evidence-based intervention or treatment protocol such as for hemodialysis applicable to this patient classification.

FIGS. 12-16 illustrate various embodiments of a system 100 in which embodiments of the present invention may be used. Various embodiments of a system 100 for characterizing circulatory blood volume include a first sensor 10 that acquires a first signal, a first processor 90 that includes at least one module 20, 30, 40 for processing and analyzing the first signal, and an interface 50 that generates an output 60. In the embodiment illustrated in FIG. 12, the sensor 10 is in communication with, via a wireline or wireless connection, a first processor 90 that is external to the sensor 10 and that includes at least one module 20, 30, 40 that processes and analyzes the signal to generate an output 60.

As described in greater detail below, the first sensor 10 may be any invasive or non-invasive device that includes circuitry to acquire a biological signal.

Figure 12:
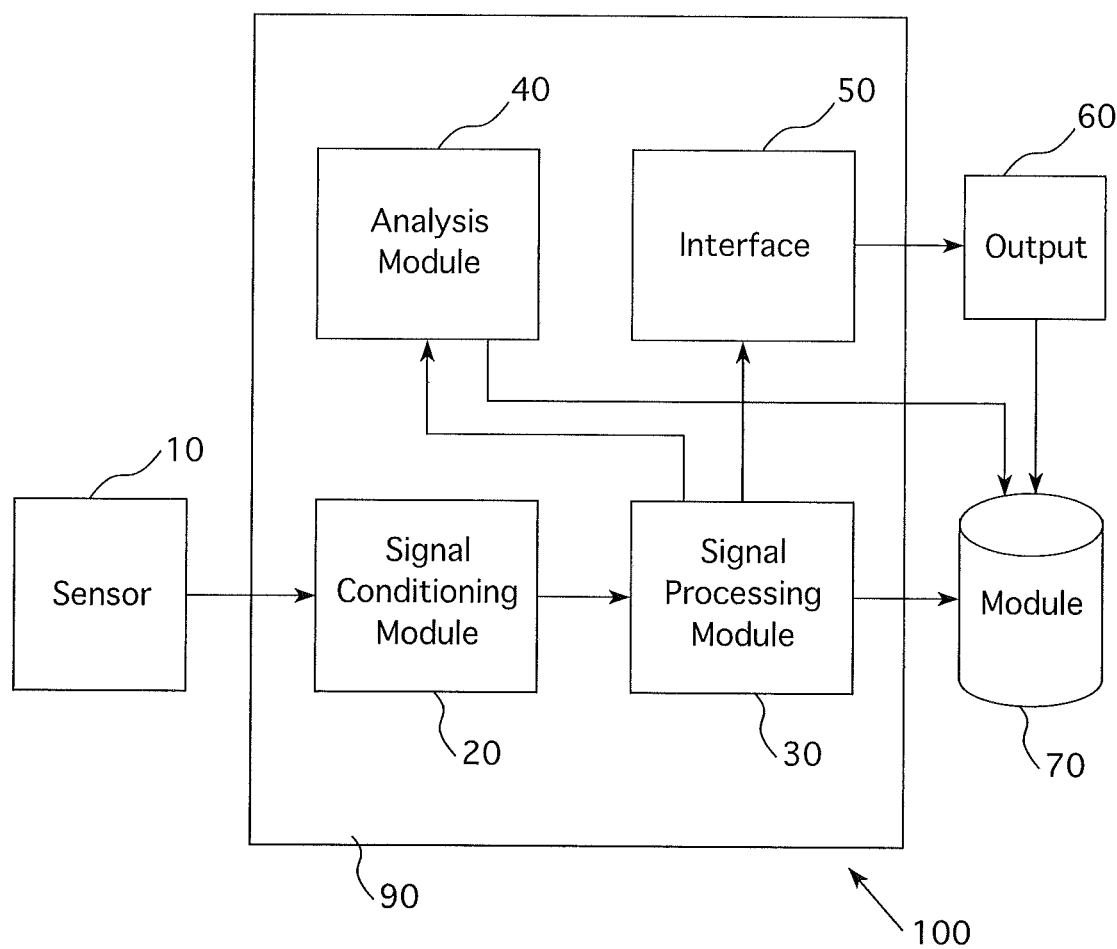
FIGS. 12-16 illustrate various embodiments of systems for characterizing circulatory blood volume.
Figure 13:
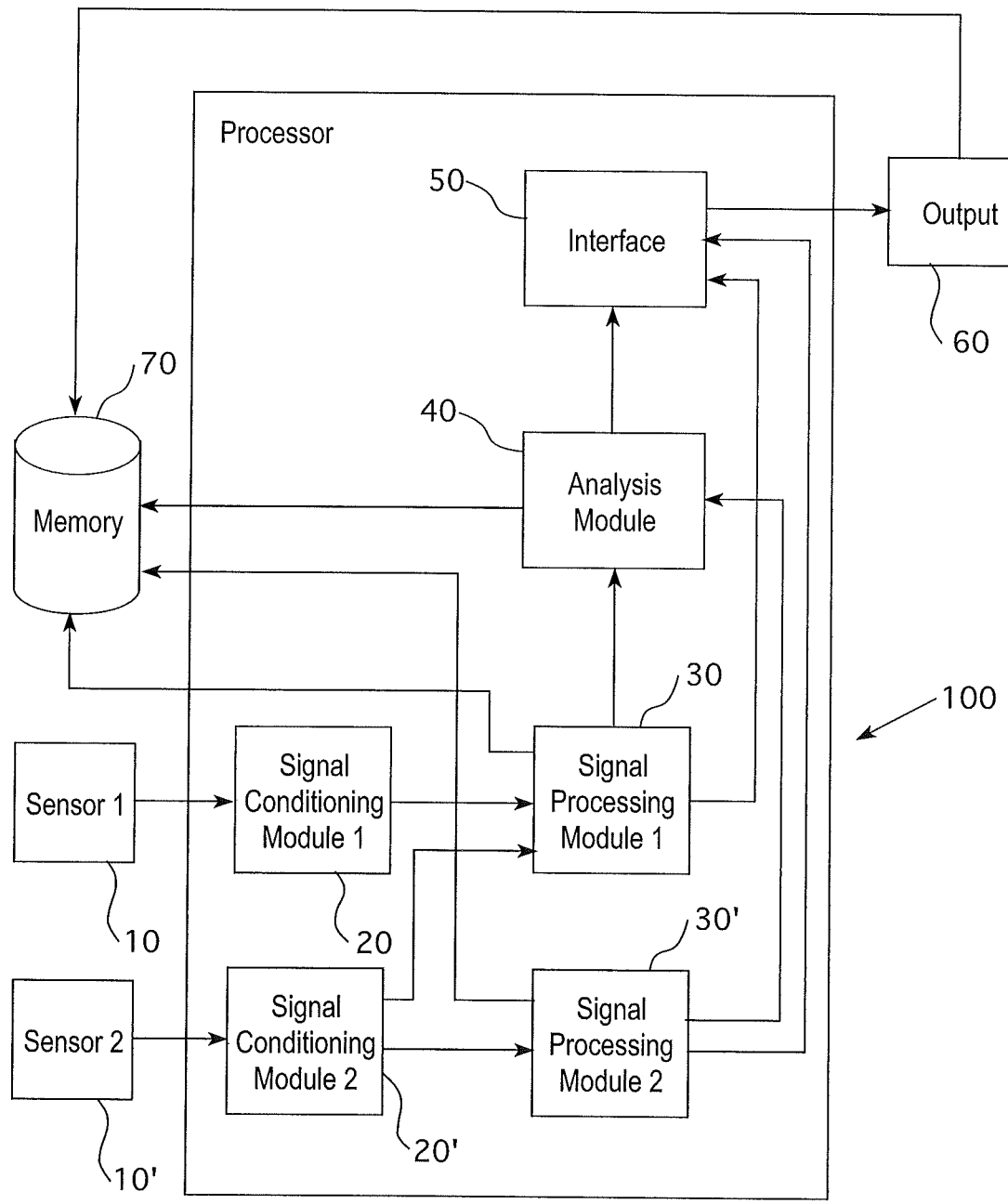
Figure 14:
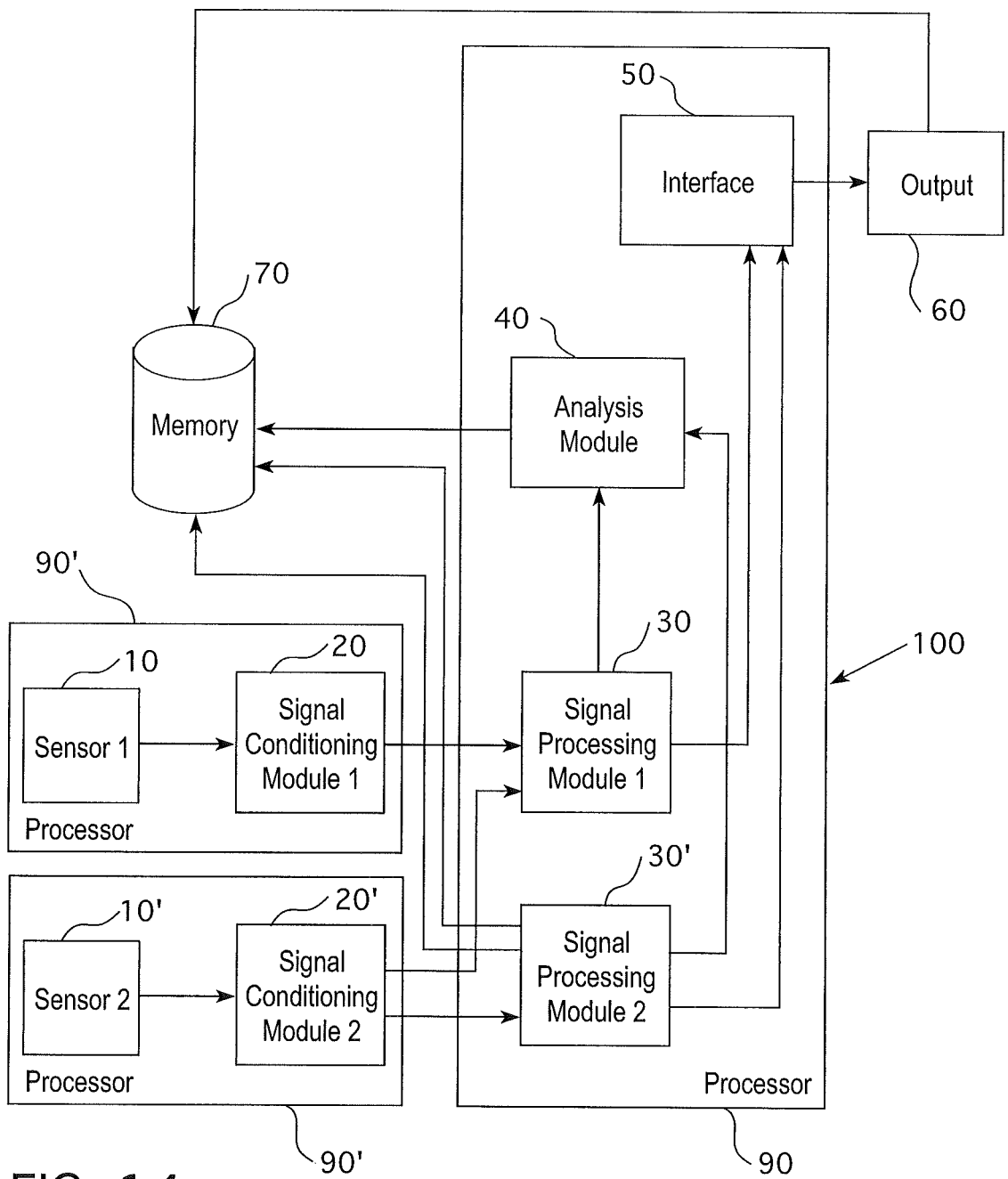
Figure 15:
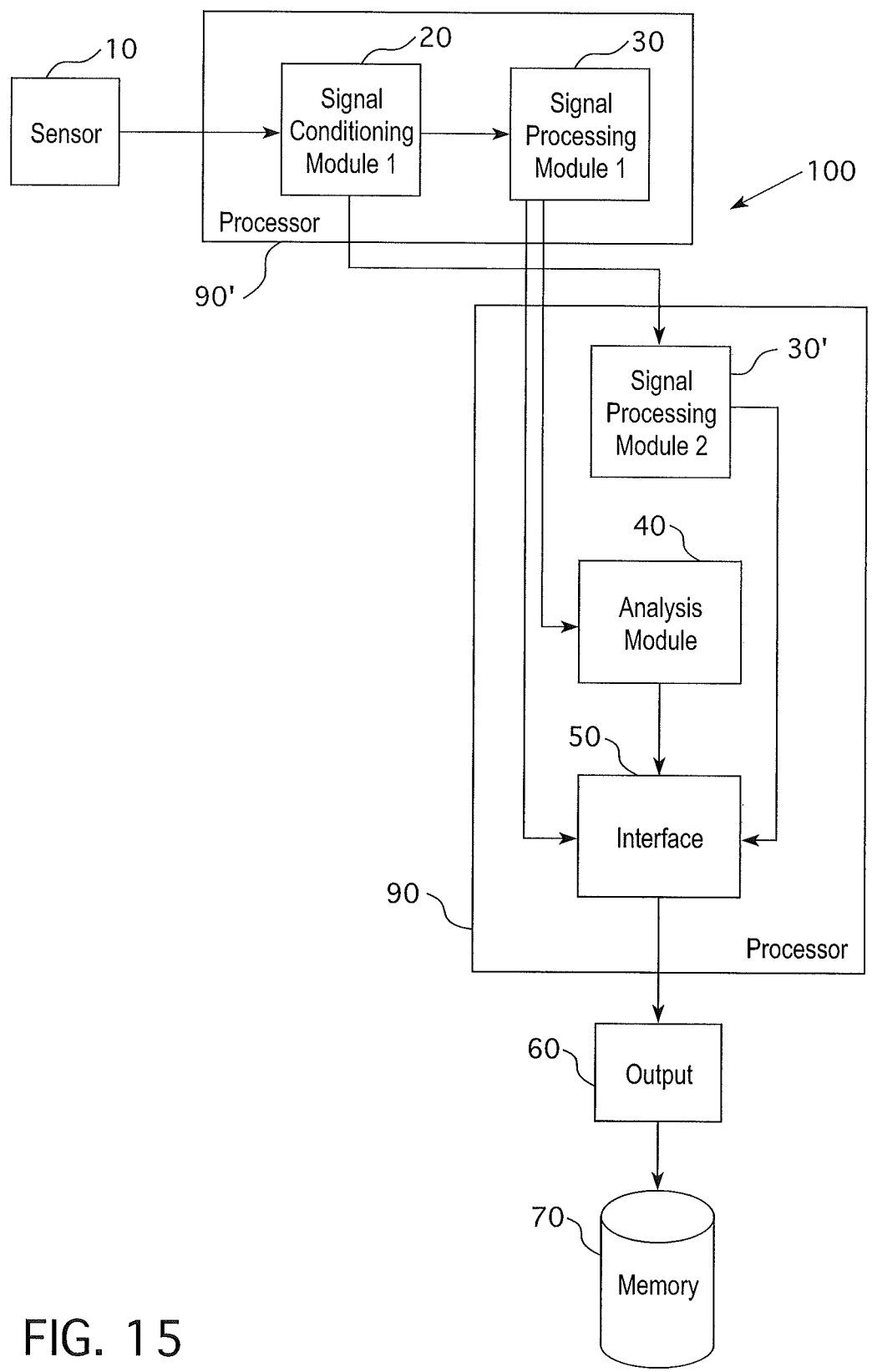
Figure 16:
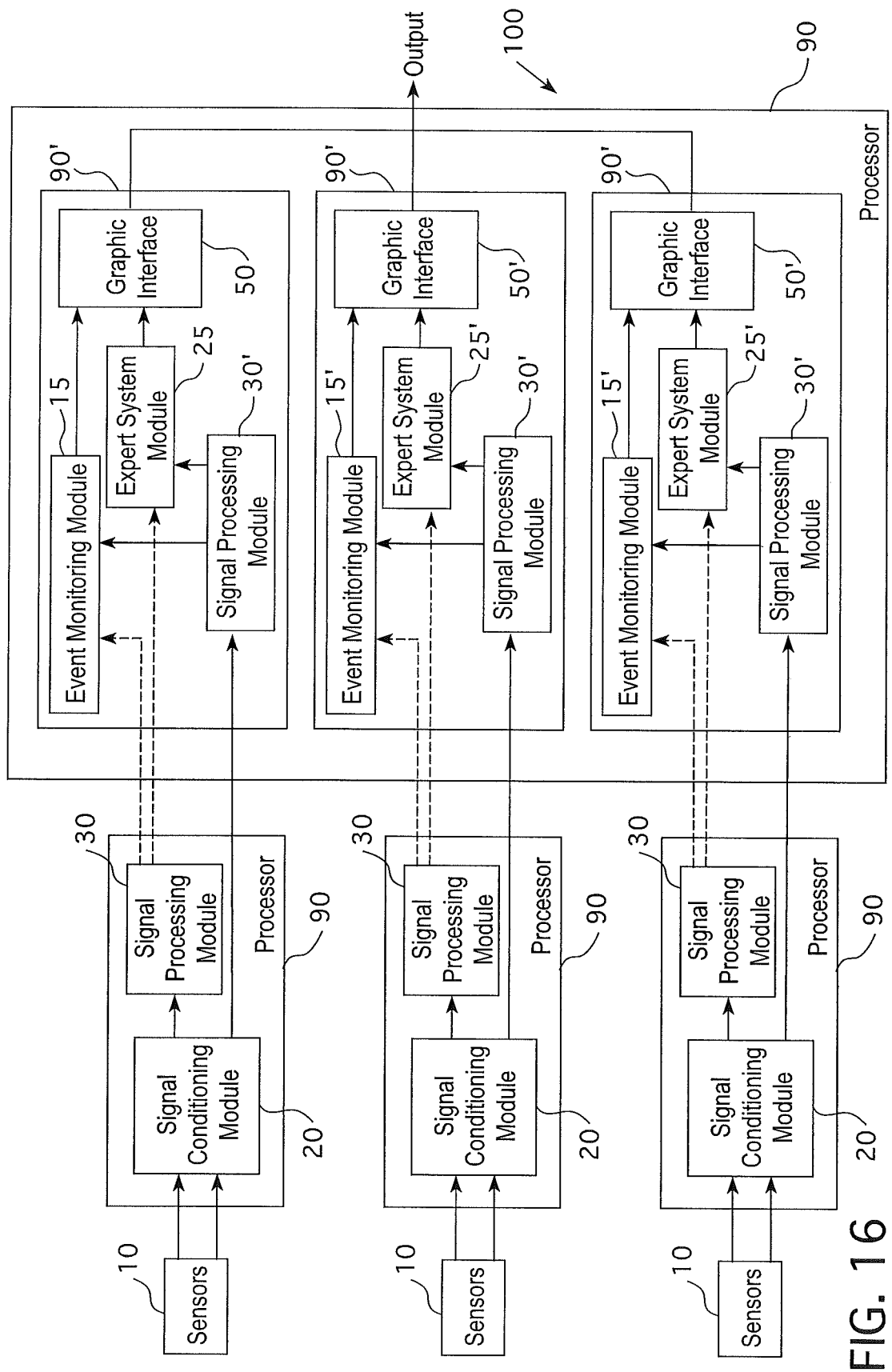

Although FIG. 12 illustrates the case of a first processor 90, it can be understood that in various embodiments, the system may include one or more second processors 90', as illustrated in FIGS. 14-16. As illustrated in FIG. 16, the second processor 90' may be collocated with the first processor 90. As illustrated in FIGS. 12-13, 16, the second processor 90' may be external to the first processor 90 and optionally may be located within the first sensor 10, and may include at least one module 30 configured for post-acquisition processing of the first signal and that communicates, via a wireline or wireless connection, with the first processor 90 for further processing of the signal prior to generation of an output 60.

Although FIG. 12 illustrates the case of a first sensor 10, it can be understood that the system 100 may include at least one second sensor 10' configured to record at least one second signal, as shown in FIGS. 13, 14, 16. In various embodiments, as illustrated, the second sensor 10' communicates with the first processor 90, via a wireline or wireless connection, to transmit the second signal to the first processor 90 for post-acquisition processing and analysis by modules 20, 30, 40 collocated therein. In various embodiments, the second sensor 10' may include a second processor 90' that includes at least one module 20', 30', 40' configured to process the acquired signal.

In various embodiments, at least one module 20, 30, 40 is in communication via, for example, wireline or wireless connections, with a graphic interface 50.

The system further includes a memory 70, such as a database or a computer readable medium. An output device 60 is in communication with the processor.

Table 1 provides a list of examples of sensors 10, 10' and the primary signal captured from each. This list is exemplary only and is not intended to be inclusive.

TABLE 2

Primary Sensors and Primary Signals.

| Primary Sensor | Primary Signal Acquired |
|---|---|
| Photo-optic sensor (transmissive) | Blood density |
| Photo-optic sensor (reflective) | Blood density |
| Pressure transducer | Pulse pressure |
| Tonometry device | Vascular palpation |
| Strain gauge | Vessel circumference |
| Ultrasound device | Vessel diameter |
| Electrical impedance | Fluid electrical conductivity |
| Radar device | Cardiac pulses |

In various embodiments, tine primary sensor 10 is a photo-optic sensor that acquires a photo-optic signal as described above. The photo-optic sensor may acquire the signal at a wavelength at which density changes reflect changes in density of both oxygenated and deoxygenated blood. In embodiments, the photo-optic sensor acquires the signal at wavelengths between about 700 nm and about 950 nm.

The photo-optic sensor may be either transmissive or reflective. In various embodiments, the photo-optic sensor is a reflective photo-optic sensor. The pulsatile and non-pulsatile portions of the photo-optic signal are illustrated in FIG. 17. The transmitter and the receiver are separated by a distance. In embodiments, the reflective photo-optic sensor is positioned on a patient's forehead or the like. In other various embodiments, the photo-optic sensor is a transmissive photo-optic sensor. In embodiments, the transmissive photo-optic sensor is positioned on a patient's finger or the like and light is transmitted through the finger or the like to a receiver on the other side of the finger.

In various embodiments, the primary sensor 10 is a pressure transducer that acquires a pulse pressure signal that indicates pulsatile changes in total blood volume. In embodiments, the pressure transducer is non-invasive. In other embodiments, the pressure transducer receives the pulse pressure signal from an arterial pressure line implanted in an artery.

In various embodiments, the primary sensor 10 is a tonometry device that acquires a signal that measures changes in vascular tension or pressure that result from changes in blood density that occur as the pulse wave travels through the arterial bed. In embodiments, tissue is applanated to obtain the vascular pressure change.

In various embodiments, the primary sensor 10 is a strain gauge that acquires a signal that measures changes in the circumference of an extremity that result from changes in blood density that occur as the pulse wave travels through the arterial bed.

In various embodiments, the primary sensor 10 is an ultrasound device that acquires a signal that measures changes in the diameter of a blood vessel that result from changes in blood density that occur as the pulse wave travels through the arterial bed.

In various embodiments, the primary sensor 10 is an electrical impedance device that acquires a signal that measures changes in electrical conductivity of the blood that result from changes in blood density that occur as the pulse wave travels through the arterial bed.

In various embodiments, the primary sensor 10 is a radar device that acquires a signal that measures changes in contraction of the cardiac muscle during a cardiac cycle.

In embodiments, the system includes at least one secondary sensor 10', as illustrated in FIGS. 13, 14, 16. Secondary sensor 10' may be any invasive or non-invasive device that includes circuitry to acquire a secondary signal. Secondary sensor 10' includes a controller and circuitry configured to acquire a secondary signal that denotes the initiation and termination of an event. In embodiments, use of secondary sensor 10' in conjunction with the primary sensor 10 enables circulatory blood volume to be characterized before, during and after an event. In embodiments, secondary sensor 10' is an accelerometer that measures a patient's axial changes such as when a patient goes from a supine to a sitting to a standing position. A system such as the one shown in FIG. 16 is useful in a clinical setting where multiple patients are being monitored. A primary sensor 10 is attached to each patient and records a biological signal. Each primary sensor 10 is in communication with, via a wireline or wireless connection, a first processor 90 that is external to the sensor 10 and that includes at least one module 20, 30, that processes the signal. In an alternate embodiment, the primary sensor 10 is in communication with, via a wireline or wireless connection, a second processor 90' that includes at least one module 20', 30' that processes the signal. In this embodiment, the second processor 90' is configured to receive signals from each primary sensor 10, each recording a signal from a different patient, and to process each signal and generate an output 70 that is useful to the clinician monitoring the circulatory blood volume of each of these patients.

Figure 18:
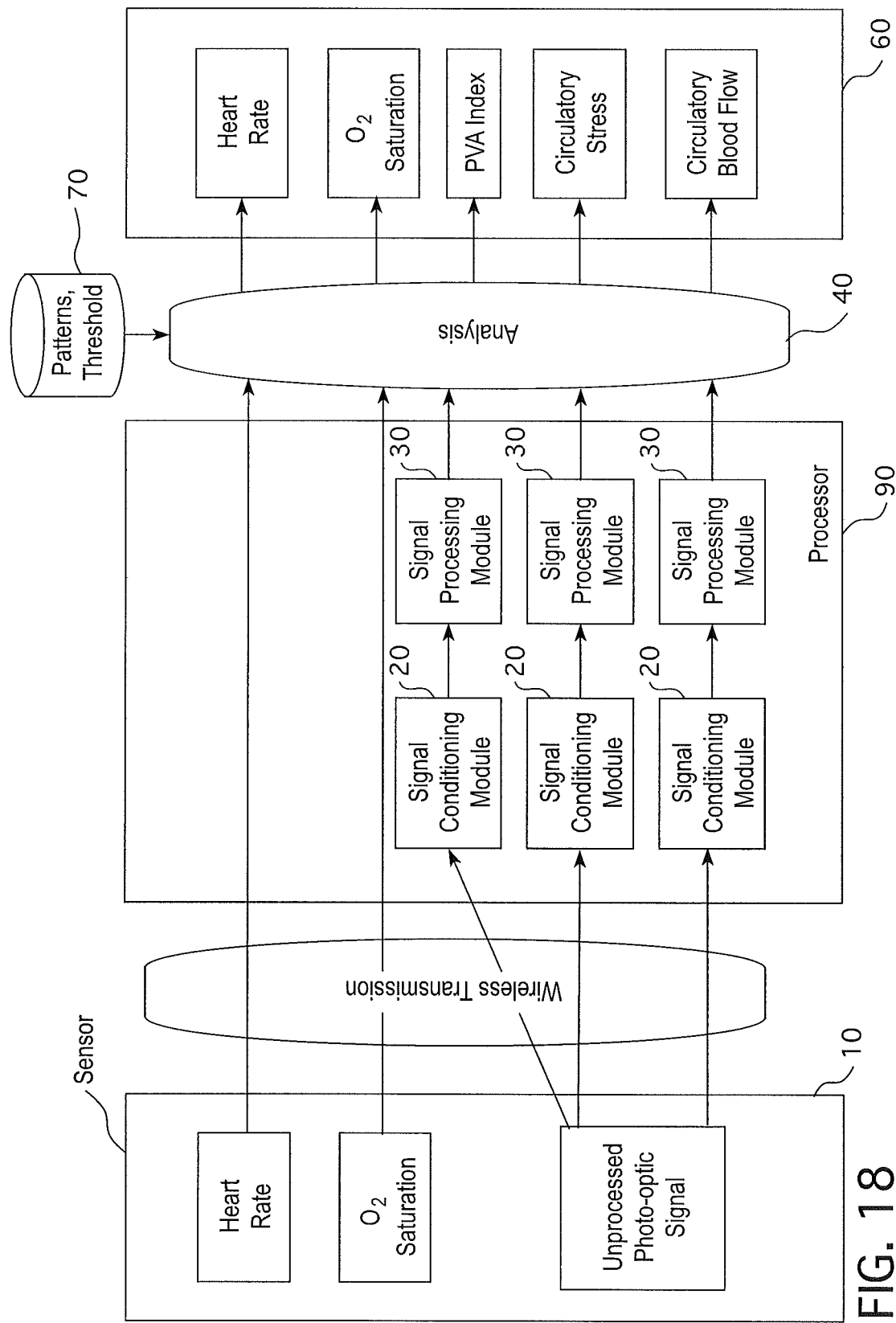
FIG. 18 illustrates an embodiment of the system used in conjunction with other sensors to characterize circulatory blood volume.

In other embodiments such as the system shown in FIG. 18, sensor 10 includes circuitry to acquire a secondary signal that measures secondary parameters such as, for example, oxygen saturation, heart rate, or core body temperature (not shown). The processor 90 includes modules 20, 30 to condition and process the biological signal and the analysis module 40 analyzes the biological signal and secondary parameters to evaluate circulatory blood volume and to generate an output 70.

In another embodiment, secondary sensor 10' is a thermocouple used to measure changes in cutaneous circulatory blood volume in order to remove the cutaneous contribution to the frequency strength measure that subsumes contributions from both the cutaneous and subcutaneous circulatory blood volume when a photo-optical sensor is placed on the skin. In another embodiment, the secondary sensor 10' is a thermocouple used to measure changes in cutaneous circulatory blood flow to calibrate the reduction or increase in autoregulatory capacity resultant of the diversion or decrease of circulatory blood volume to the skin due to thermal regulation.

In various embodiments, the secondary sensor 10' is an electrodermal sensor that provides a qualitative measure of cognitive stress that may be used to calibrate the impact that cognitive stress has on the patient's autoregulatory capacity to maintain homeostasis.

Various embodiments of the present invention may be implemented on non-transitory computer-readable media. The terms "computer-readable medium" and "computer-readable media" in the plural as used herein may include, for example, magnetic and optical memory devices such as diskettes, compact discs of both read-only and writeable varieties, optical disk drives, hard disk drives, and the like, all of which may store non-transitory signals. A computer-readable medium may also include memory storage that can be physical, virtual, permanent, temporary, semi-permanent and/or semi-temporary.

EXAMPLES

The following examples illustrate several embodiments of the claimed chromatography column. These examples should not be construed as limiting.

FIGS. 19-22, 24, and 25 illustrate data collected using systems and methods embodying the present invention.

Example 1

The combination of the derived parameters circulatory stress and circulatory blood volume can be used to predict and recognize circulatory blood volume adequacy. In Example 1, a Lower Body Negative Pressure Chamber was used to simulate circulatory blood volume loss. A human patient was placed into a sealed pressure chamber that comes up to just below the rib cage. A vacuum was used to decrease chamber pressure having the effect of sequestering blood to the feet and pulling it out of circulation. As shown in FIG. 19A, pressure in the chamber was held at zero mm Hg, then was decreased in 5 steps of −10 mm Hg each and held for 3 minutes per step, and then was returned back to zero mm Hg. Sensor 10 was positioned on the patient's forehead to record the biological signal from which the derived parameters, circulatory stress and circulatory blood volume values were calculated according to the method shown in FIGS. 5-9, described above. Percent change in the derived parameters were plotted over time, as shown in FIG. 19B. FIG. 19C shows the systolic blood pressure of the patient, recorded using a Finapres. All graphs shown in FIGS. 19A-C are aligned vertically in time.

Figure 19:
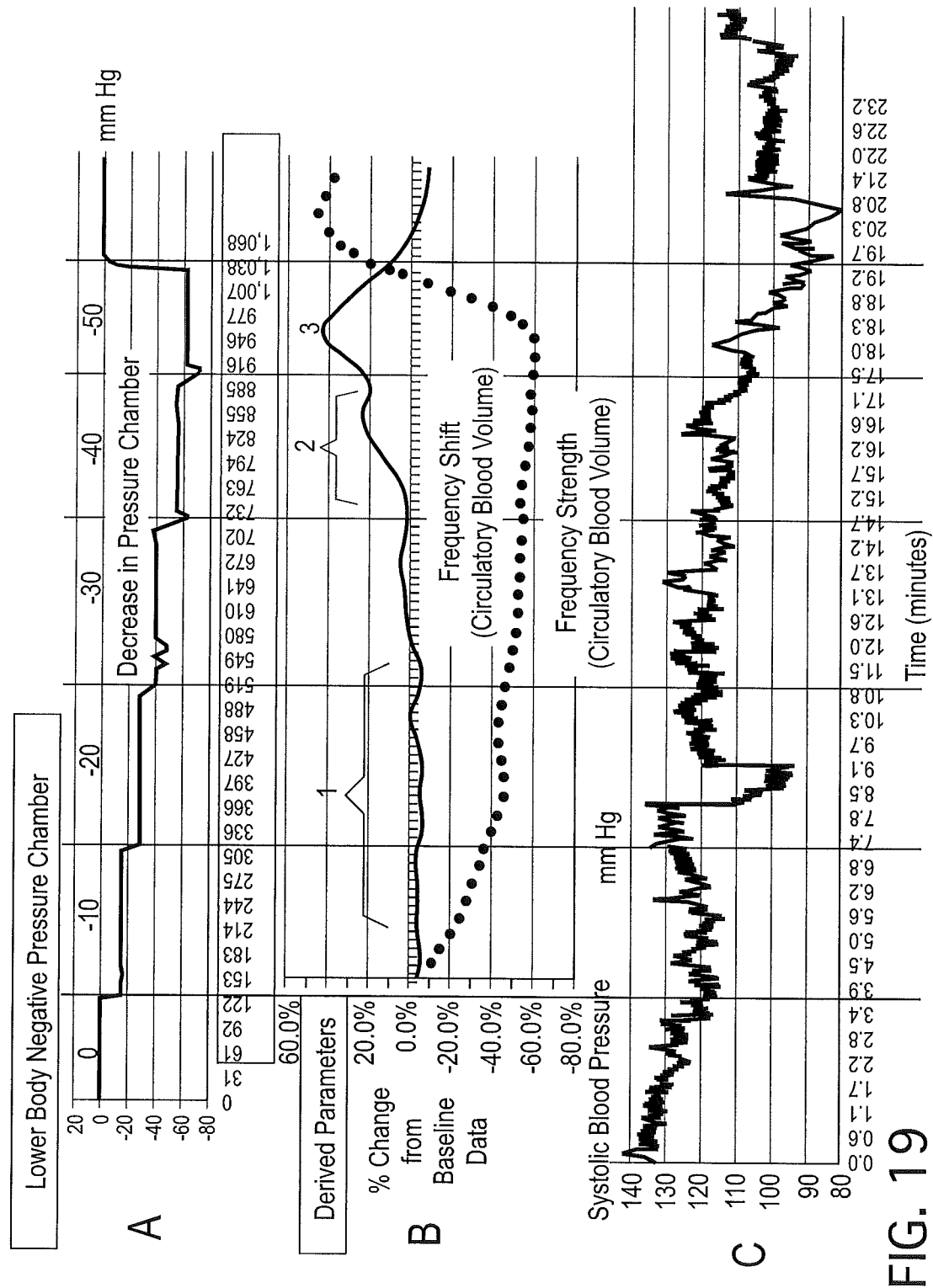
FIGS. 19-22 illustrate various examples of data collected using embodiments of the systems and methods.
Figure 20:
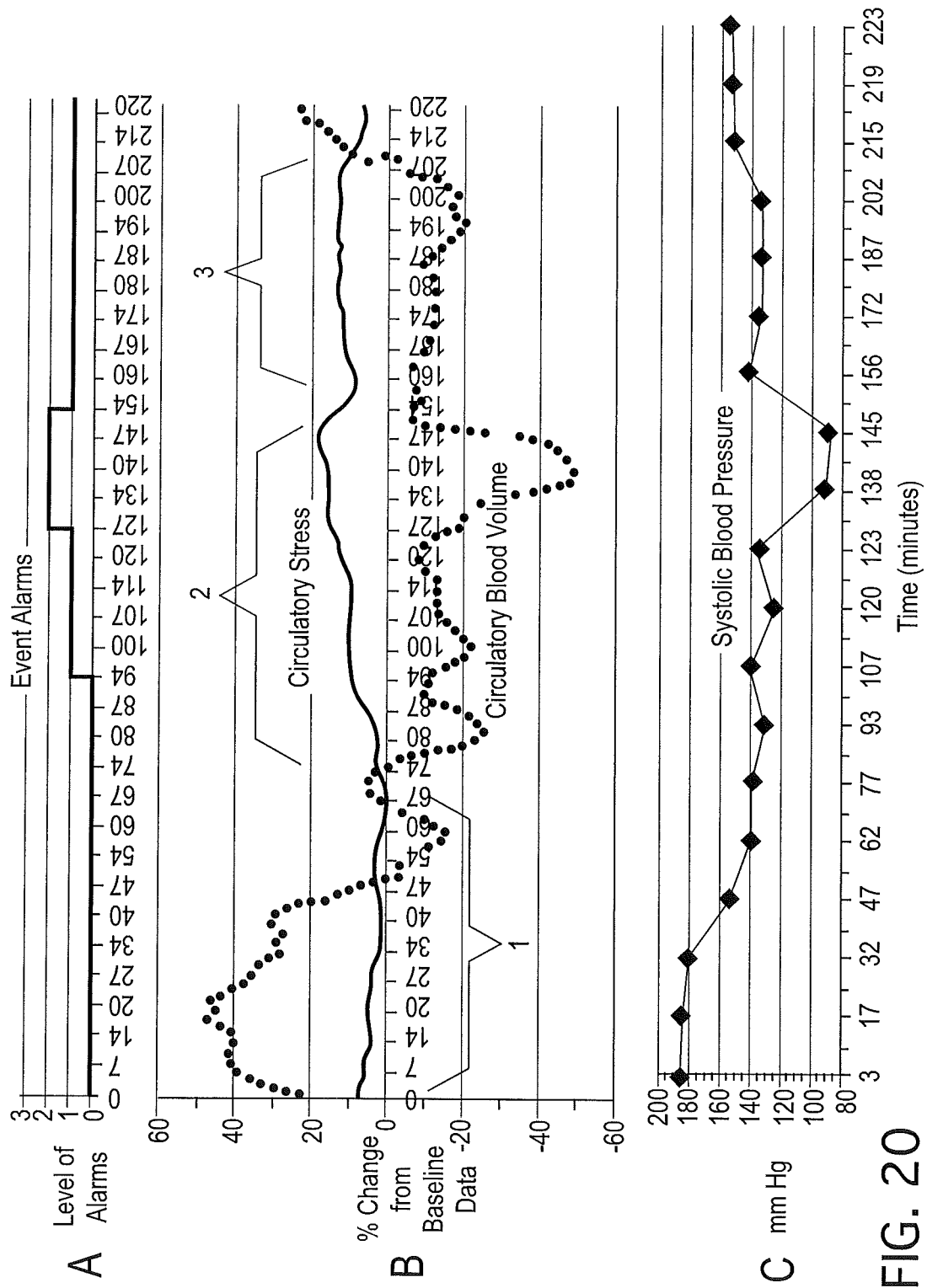
Figure 21:
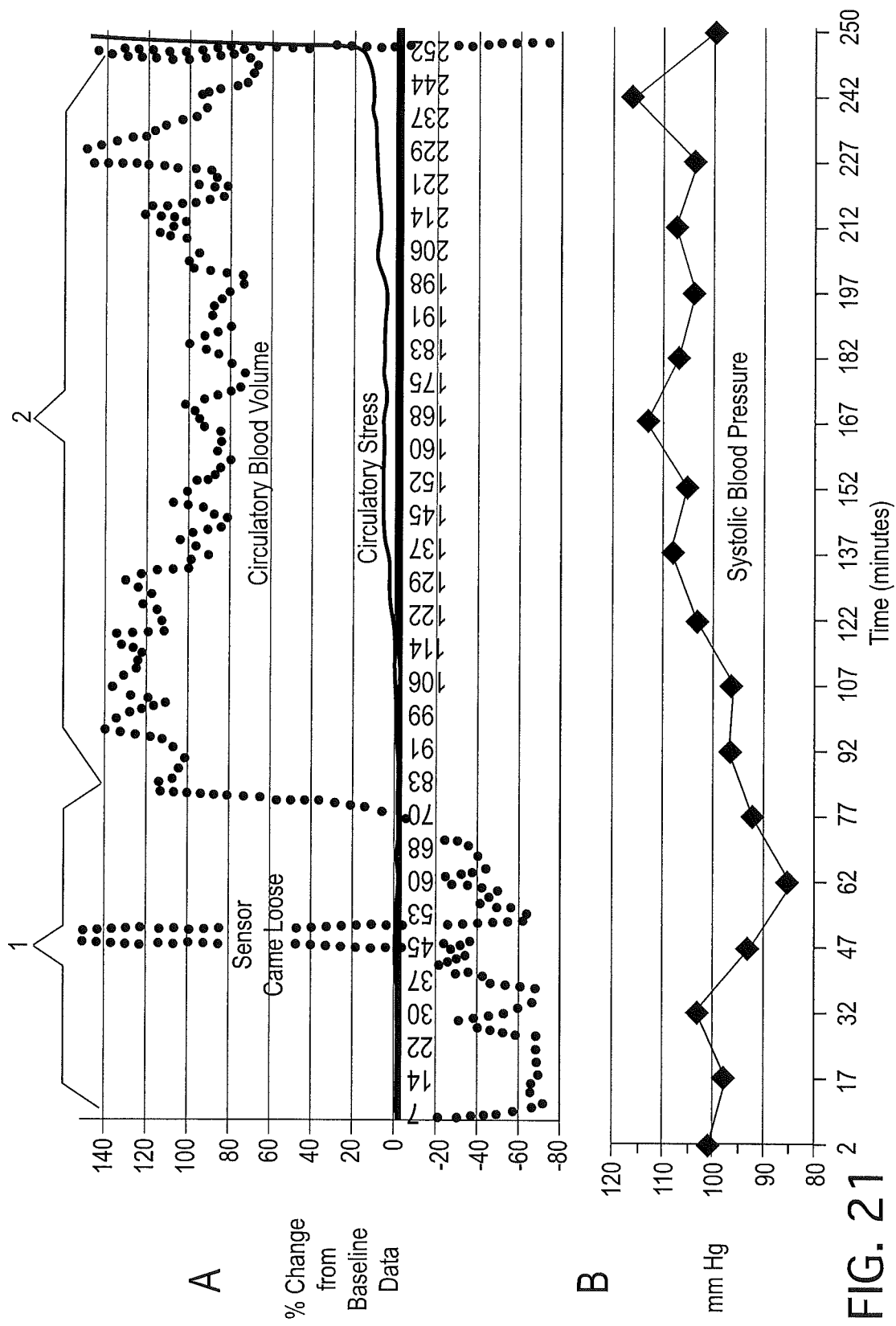

Periods 1, 2, and 3 are depicted in FIG. 19. Referring to FIG. 19B, during Period 1, the subject's compensatory mechanisms were adequately adapting to the reduction in circulatory volume as indicated by the minimal percentage change in circulatory stress. However, also in Period 1, there was a substantial decrease in the percentage change in circulatory blood volume, indicating a poor compensatory capacity during this initial low stress period of the test. As pressure in the chamber was further decreased, the percentage change in circulatory stress began to increase, indicating the beginning of inadequate compensation corresponding with a further decline in the percentage change in circulatory blood volume being maintained by the autoregulatory mechanisms.

During Period 2, the sharp rise in the percentage change in circulatory stress indicates a more pronounced compensatory inadequacy to accommodate the continued loss of blood volume from the circulatory system. During this same period, the percentage change in circulatory blood volume was not decreasing at the same rate as the percentage change in circulatory stress was increasing. This pattern indicates that the subject has little remaining stress capacity tolerance. In this example, in each of Periods 1-3, the derived parameters indicate an ensuing hypovolemic event and related compensatory inadequacy while symptomatic measures such as blood pressure have not yet changed. With less capacity to tolerate this simulated volume loss, indicated by a small percentage change in circulatory blood volume during Period 3, circulatory stress rapidly increases, indicating a failing cardiovascular autoregulatory function. This conclusion is reinforced by the severe drop in systolic pressure (FIG. 19C) during Period 3.

Example 2

The derived parameters circulatory stress and circulatory blood volume can be used to indicate pre-symptomatic and symptomatic conditions of circulatory blood volume inadequacy. In practice, the conditions that the derived parameters can be used to recognize are equivalent to recognizing when the patient has become intolerant to the stress of fluid removal during dialysis treatment. In example, 2 data were captured from an end-stage renal failure patient undergoing stress from accumulated fluid removal during hemodialysis employed as kidney replacement therapy. The treatment period was approximately 4 hours long and performed about three times per week. FIG. 20A illustrates the points in time at which event alarms from the device were activated. FIG. 20B illustrates the percentage change in circulatory stress and circulatory blood volume over the time of the therapy. FIG. 20C illustrates systolic blood pressure captured from a blood pressure cuff placed on the brachial artery of the arm and recorded every ~10 minutes throughout the treatment. All graphs vertically aligned in time.

The accumulation of fluid in the circulatory system causes increased blood pressure and has a pronounced load on the cardiovascular function. As fluid is removed from the circulatory system, where 8% of the total body fluid resides, the load on the cardiovascular function is greatly reduced. This is demonstrated by the rapid increase in circulatory blood volume and the decrease in circulatory stress during Period 1, illustrated in FIG. 20B. Hypertension, indicated by systolic blood pressure in Period 1 (FIG. 20C) also is reduced.

As the therapy progresses, the loss in circulatory volume causes accumulated plasma water to be drawn into the arterial tree from the interstitial and cellular compartments. If the rate of fluid removal exceeds the vascular refill rate, a hypovolemic condition then ensues. If this condition exceeds the cardiovascular compensatory mechanisms, the patient can undergo an acute hypovolemic event resulting from inadequate tissue and organ circulating blood volume. A hypovolemic progression is illustrated in Period 2 (FIG. 20B) where the circulatory blood volume rapidly decreases, suggesting a fluid removal rate that exceeded the refill rate. Compensatory inadequacy to accommodate the continued decrease in circulatory volume as the fluid removal continues is indicated by the sudden rise in circulatory stress during Period 2. Autoregulatory capacity to tolerate the current circulatory stress is denoted by the severe drop in circulatory blood volume during Period 2. Use of the inventive system and method, which identify these changes in the derived parameters, trigger an event alarm (FIG. 20A) well in advance of the time at which the drop in systolic blood pressure occurs indicating autoregulatory failure.

During Period 3, the fluid removal rate has been reduced and eventually stopped at the end of period 3. This corresponds to the decreased percentage change in circulatory stress value and restoration of the circulatory blood volume, indicating that the fluid refill combined with autoregulatory mechanisms have adequately addressed the impaired circulatory blood volume that occurred during Period 2. Again, this observation is reinforced by the restoration of the systolic blood pressure during Period 3.

Example 3

Patterns of response based on circulatory stress and circulatory blood volume can be used to recognize specific pathologies and to assess cardiovascular functional health. When a patient having compromised cardiovascular function undergoes therapy, the derived parameters may be used to identify a dosage endpoint. The data shown in FIG. 21 were collected from a patient having both end-stage renal failure and right-sided heart failure and who underwent hemodialysis therapy lasting approximately 4 hours. Heart failure refers to a condition where the heart muscle becomes progressively weakened resulting in a degraded cardiovascular compensatory capacity. When fluid is accumulated in an end-stage renal failure patient who also suffers from heart failure, the weakened heart has difficulty pumping volume against the increased load from the accumulated fluid at the output of the left ventricle.

As the heart failure patient attempts to adapt to the stress from the hemodialysis treatment, the weakened heart confronted with hypertension from the accumulated circulatory volume has difficulty adapting to this stress and the percentage change in circulatory blood volume immediately drops during Period 1 (FIG. 21A). However, during Period 1, circulatory stress remains in a steady state, indicating the patient is not in danger of an acute hypovolemic condition. As soon as an adequate amount of the accumulated fluid and its corresponding load on the heart has been reduced, the percentage change in circulatory blood volume dramatically increases during Period 2 (FIG. 20A) as does the systolic blood pressure (FIG. 20B) as the pumping function of the heart is restored. There is a steady increase in the percentage change in circulatory stress throughout the remainder of the treatment but due to the low level of this stress. There is no compensatory inadequacy portrayed as shown by the modest increase in the percentage change in circulatory stress.

The ability to provide a non-invasive, low risk methodology to recognize heart failure behavior is very valuable. The only alternative means to recognize hemodynamic behavior for heart failure is by measuring the ejection fraction of the heart by inserting a Swan Ganz catheter in one of the heart chambers. Recognition in changes of cardiovascular autoregulation due to the decline of the heart function in heart failure patients is referred to as decompensating heart failure and leads to poor circulatory volume adequacy and failing organ and tissue functions. Use of this technology to recognize cardiovascular autoregulatory changes when challenged by a standardized stress such as a sitting-to-standing maneuver, lying-to-sitting, or passive leg raise maneuver is valuable. In one embodiment, a standardized test such as a passive leg raise maneuver, can be used to assesses the preload and afterload dependency on the cardiac function resultant of the stress from the leg raise. Similarly, once the cardiovascular system has adapted to this increased transient thoracic volume, a leg lower can be used to assess the autoregulatory or compensatory capacity of the cardiovascular function. In another embodiment, collecting responses to a physical maneuver over time can be used to identify early signs of autoregulatory changes such as cardiovascular decompensation. This can be used to determine whether the current heart function was functioning adequately to support a normal level of physical stress experienced during independent living. Given that patient observation is not required to perform a standardized stress test and that values from the test may be obtained remotely, use of this device and method provide a pre-symptom, sensitive, and pathology—specific test to recognize and manage chronic heart failure patients remotely as part of a telemedicine communications configuration.

Example 4

The inventive system and method, in combination with a stress such as dialysis treatment or a standardized physical maneuver, may be used to assess and manage the appropriateness of the measured autoregulatory response. This technique may be used to assess changes in the functional performance of the autoregulatory mechanisms and/or to manage pharmaceuticals that are used to treat hypertension and other cardiovascular diseases or dysfunctions that often have an effect on autoregulatory function, thereby altering the compensatory mechanisms.

Figure 22:
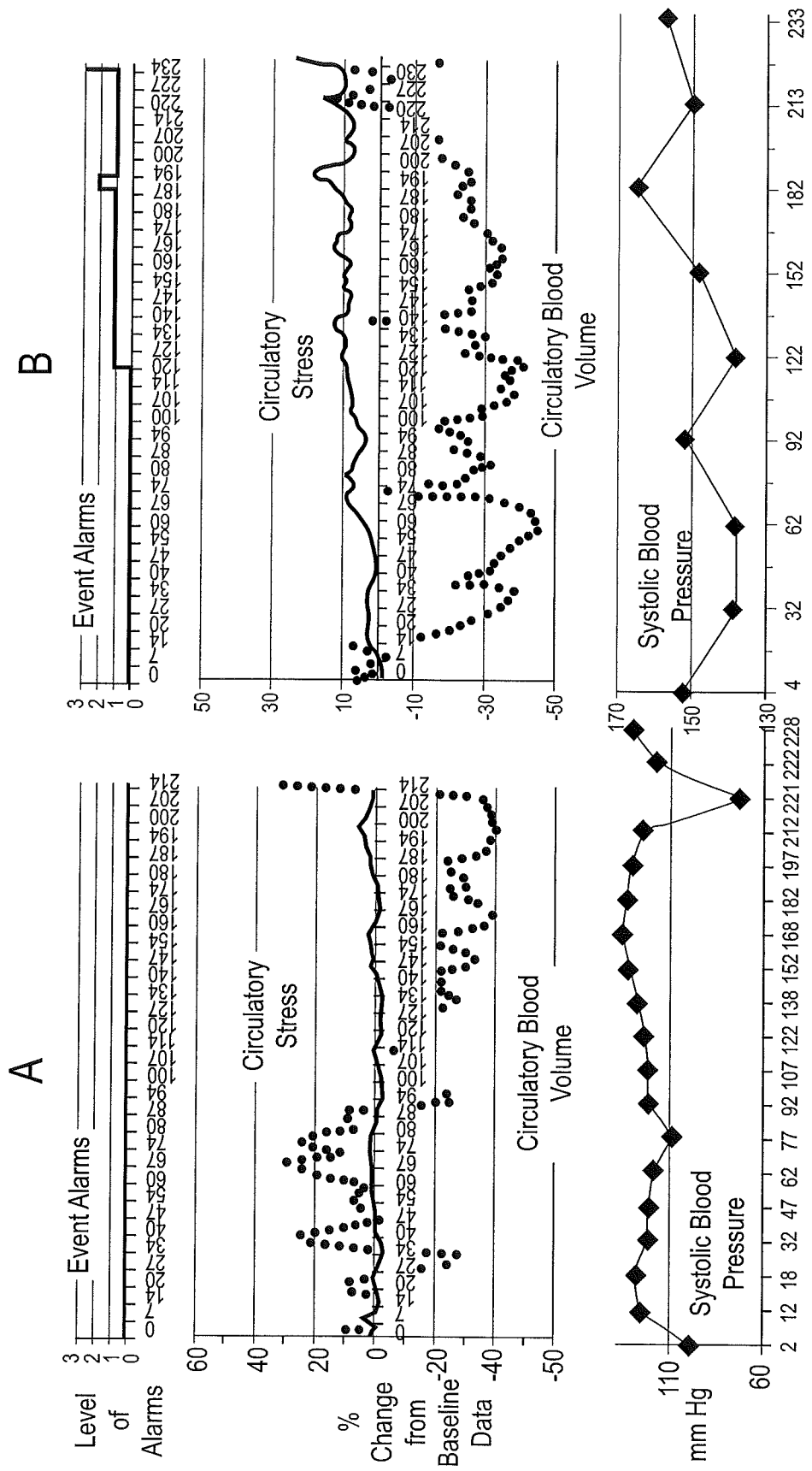

FIG. 22 illustrates data collected over approximately a four hour time period from a hypertensive end-stage renal failure patient undergoing hemodialysis treatment. Graphs illustrated in FIG. 22A show the patient's response to fluid removal while under the influence of a high dosage of beta-blockers, which had a blunting effect on the autoregulatory response. There was little change in the percentage change in circulatory stress throughout the four hour treatment even though the patient was experiencing nausea and light-headedness, symptoms of inadequate circulatory blood volume and autoregulation. Blood pressure (FIG. 22A) remained relatively stable throughout the treatment. Additionally, when the patient stood at the conclusion of the treatment (designated by the *), blood pressure dropped, also indicative of a poor autoregulatory function.

Data illustrated in FIG. 22B were captured during a follow-on dialysis treatment several days later after the beta-blocker dosage was reduced in half. The percentage change in circulatory stress is more dynamic and responsive throughout the treatment. Similarly, the percentage change in circulatory blood flow is also more dynamic indicating a more responsive autoregulation of the circulatory blood volume.

Examples 5 and 6

Figure 24:
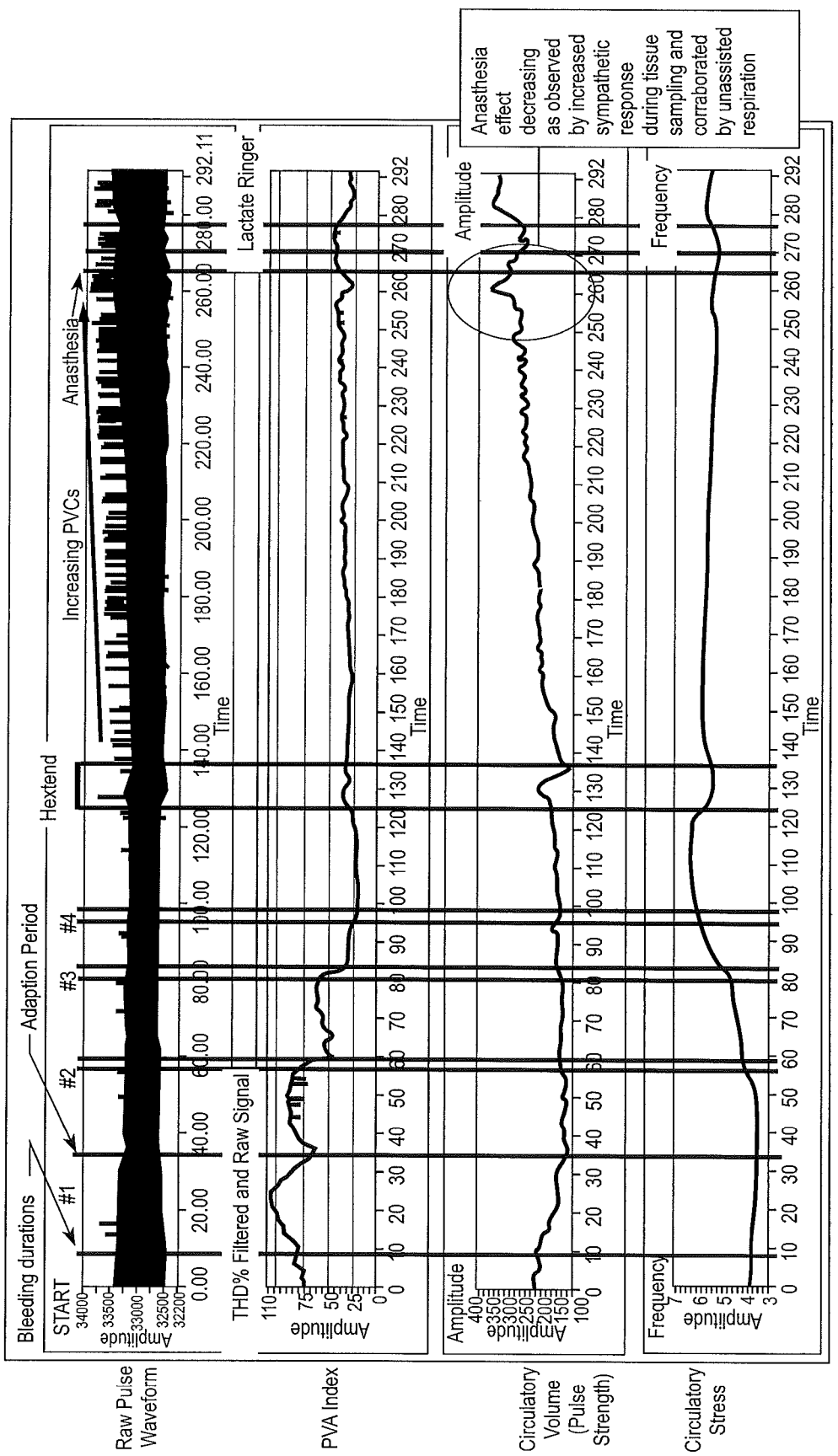
FIGS. 24 and 25 illustrate examples of data collected using embodiments of the systems and methods.
Figure 25:
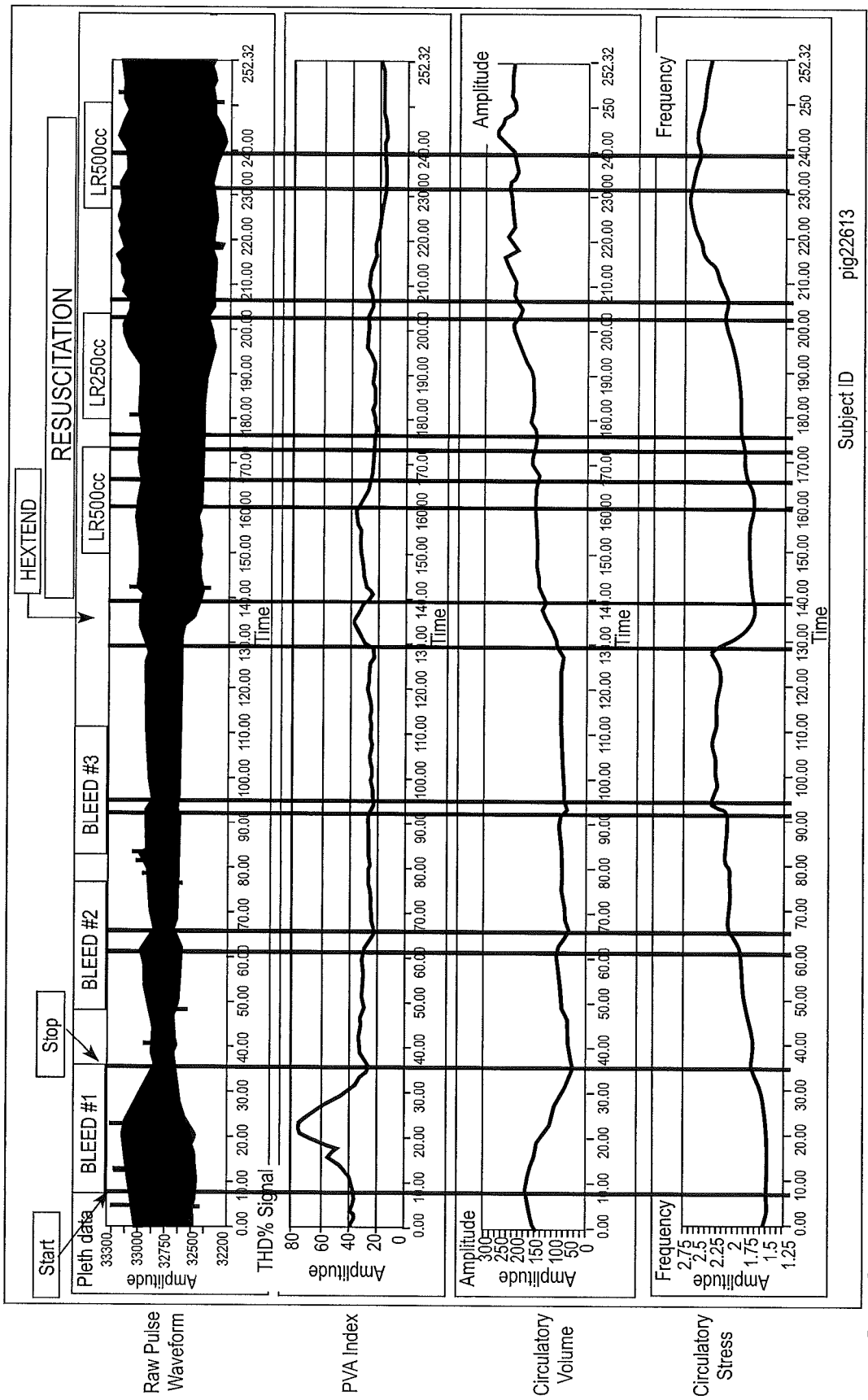

FIGS. 24 and 25 illustrate examples of data collected using a total harmonic distortion as described in connection with FIG. 23. The example illustrated in FIG. 24 is an example where embodiments of the present invention are used to manage anesthetic and fluid for resuscitation or during acute care. The illustrated example is a porcine example that demonstrates the effects of exsanguination. The total harmonic distortion (THD) p waveform portrays alterations in the frequency strength of the harmonics in proportion to frequency strength of the fundamental heart rate frequency resultant of the effects of compliance changes in internal branch of the carotid artery on the forehead where the sensor is placed. An initial increase in the THD ratio portrays initial increase in compliance at the start of the bleed followed by an decrease in compliance to adapt to blood loss. As illustrated in FIG. 24, the PVA Index shown as the total harmonic distortionwaveform portrays the effects of increases or decreases in overall circulating blood volume, the effects of circulatory blood volume viscosity or oxygen carrying capacity resultant of transfusion of blood additives such as Hextend that can thin the blood and/or reduce the hematocrit density resulting instiffening of the arterial tree to compensate for these changes that then results in decreasing the harmonics of the cardiac pulse wave.

At minute 260 in FIG. 24, the effects of the anesthesia wear off and the pig becomes more sensitive to cutting of tissue (see increase in effective volume). As another embodiment, the recognition of increased sympathetic responses during surgery can be used as feedback to titrate the appropriate level of anesthetic. In this example, the anesthesia is increased to reduce the effects, but the anesthesia dilates the blood vessels and blunts the nervous system. This results in the effective volume being reduced primarily due to the dilation effect. Lactate ringers were then administered to bring the fluid levels up to level prior to the additional anesthesia being administered.

The pulse oximetry in FIG. 24 indicates the amount of oxygenation at any moment in the blood. The pulse wave form is a measure of the density of total red blood cells (oxygenated and deoxygenated hemoglobin) in the underlying arterial bed from the changes in absorption of the near infrared frequency. As illustrated in FIG. 24, the relative changes of the red blood cells from a baseline value in the first 7 minutes indicates that, when red blood cells are diluted through transfusion, the effective circulatory volume (or pulse strength) signal indicates how well the cardiovascular system is able to maintain a constant perfusion of red blood cells in the tissue. Such a scenario comes at the cost of increasing heart rate in order to circulate the diluted red blood cells faster.

FIG. 25 illustrates another porcine example. Data has indicated that a normal circulatory volume level is represented by a PVA Index portrayed as the total harmonic distortion measure of approximately 40%, and thus such a measure may be used to recognize whether an individual is either volume loaded or volume deficient (e.g. dehydrated). As shown in FIG. 25, the total harmonic distortion level begins at a value of 40%. As described herein, the total harmonic distortion value can show decreases due to blood loss as illustrated in FIG. 25 where the total harmonic distortion value increases as the subject pig is initially bled from the 10 minute mark to the 20 minute mark. The PVA Index (total harmonic distortion value) can also show the effects of the compensatory mechanisms of vasoconstriction of the small arteries indirectly even when placed on top of a large artery resultant in the pulse strength alterations resultant in a systemic change in circulatory blood volume when peripheral vasoconstriction occurs. In this example, even though the subject pig in FIG. 25 is still being bled at the same rate, when the total harmonic distortion value approaches minute 25 it begins to decrease, indicating that the walls of this large artery are becoming more stiff (less compliant), a compensatory related change. The circulatory volume change is further confirmed by the decrease in the relative measure of circulatory volume shown in this figure as "frequency strength".

After the bleed, the PVA Index (total harmonic distortion value) reaches a new steady state but circulatory volume increases as fluid is transferred from other compartments to compensate for the blood loss. Given that only 5-10% of the volume of the body is in the arterial tree, one defensive mechanisms is to transfer volume over time from venous reserves or diversion from the circulatory flow from the organs or tissues into the arterial tree to defend against arterial volume loss.

A clinician thus may see the dynamics related to defensive mechanisms when looking at the PVA Index. When viewed in conjunction with the circulatory volume (amplitude), a clinician may see the effectiveness of these mechanisms in restoring or compensating for circulatory volume loss.

The frequency signal in FIG. 25 represents changes in heart rate of the subject pig. Changes indicate circulatory stress and the signal may be used to indicate the severity of the volume deficiency challenge on the cardiovascular compensatory mechanisms, thus providing a more complete picture of how much difficulty the patient is having with circulatory changes at any point in time.

While several embodiments of the invention have been described, it should be apparent that various modifications, alterations, and adaptations to those embodiments may occur to persons skilled in the art with the attainment of some or all of the advantages of the present invention. It is therefore intended to cover all such modifications, alterations, and adaptations without departing from the scope and spirit of the present invention.

What is claimed is:

1. A method for characterizing a circulating blood volume, the method comprising:
   receiving, by a computing device, a biological signal emulating an arterial pulse wave from a sensor associated with a human body;
   calculating, by the computing device, a plurality of integer harmonics of a heart rate from the biological signal, wherein each of the plurality of integer harmonics is characterized by an integer harmonic amplitude;
   calculating from the plurality of integer harmonic amplitudes of the heart rate, by the computing device, at least one derived parameter in a frequency domain comprising a measure of total harmonic distortion; and
   characterizing the circulating blood volume by comparing, by the computing device, the at least one derived parameter to a baseline value.

2. The method of claim 1, wherein the sensor comprises one or more of the following:
   a transmissive photo-optic sensor;
   a reflective photo-optic sensor;
   a pressure transducer;
   a tonometry device;
   a strain gauge;
   an ultrasound device;
   an electrical impedance device; and
   a radar device.

3. The method of claim 1, further comprising:
   conditioning the biological signal to form a conditioned biological signal; and
   calculating, by the computing device, at least one second derived parameter in the frequency domain based on the conditioned biological signal.

4. The method of claim 3, wherein conditioning the biological signal comprises amplifying the biological signal or filtering the biological signal.

5. The method of claim 1, wherein calculating a plurality of integer harmonics of a heart rate from the biological signal comprises:
   sampling, by the computing device, the biological signal into a plurality of discrete data within a time window, to form windowed discrete signal data; and
   performing, by the computing device, a spectrum analysis of the windowed discrete signal data.

6. The method of claim 5, wherein performing a spectrum analysis of the windowed signal data comprises applying a Fast-Fourier Transform to the windowed signal data.

7. The method of claim 5, wherein performing a spectrum analysis of the windowed signal data comprises applying a wavelet transformation to the windowed signal data.

8. The method of claim 1, further comprising comparing a pattern of the at least one derived parameter in the frequency domain over time to a library of patterns of the derived parameter in the frequency domain over time.

9. The method of claim 1, wherein calculating the measure of the total harmonic distortion comprises summing together the integer harmonic amplitude of each of the plurality of integer harmonics of the heart rate.

10. The method of claim 1, wherein calculating the measure of the total harmonic distortion comprises:
    summing together the integer harmonic amplitude of each of the plurality of integer harmonics of the heart rate to yield a numerator, and
    dividing the numerator by an amplitude of a fundamental frequency of the heart rate.

11. The method of claim 1, wherein calculating the measure of the total harmonic distortion comprises:
    setting a denominator equal to the integer harmonic amplitude of an integer harmonic having a largest integer harmonic amplitude value among the plurality of integer harmonics of the heart rate;
    taking a square root of a sum of squares of the integer harmonic amplitudes of the plurality of integer harmonics of the heart rate except for the integer harmonic of the heart rate having the largest integer harmonic amplitude value among the plurality of integer harmonics of the heart rate to yield a numerator, and
    dividing the numerator by the denominator.

12. A method for characterizing a circulating blood volume in an animal body in a response to at least one stress, the method comprising:
    characterizing a first circulating blood volume by:
        receiving, by a computing device, a first biological signal emulating an arterial pulse wave from a sensor associated with the animal body,
        calculating, by the computing device, a first plurality of integer harmonics of a heart rate from the first biological signal wherein each of the first plurality of integer harmonics is characterized by a first integer harmonic amplitude,
        calculating from the plurality of first integer harmonic amplitudes of the heart rate, by the computing device, at least one first derived parameter in a frequency domain comprising a first measure of total harmonic distortion, and
        characterizing the first circulating blood volume by comparing, by the computing device, the at least one first derived parameter to a first baseline value;
    applying at least one stress to the animal body;
    determining a measure of a second circulating blood volume by:
        receiving, by the computing device, a second biological signal emulating an arterial pulse wave from a sensor associated with the animal body,
        calculating, by the computing device, a second plurality of integer harmonics of a heart rate from the second biological signal, wherein each of the second plurality of integer harmonics is characterized by a second integer harmonic amplitude,
        calculating from the plurality of second integer harmonic amplitudes of the heart rate, by the computing device, at least one second derived parameter in a frequency domain comprising a second measure of total harmonic distortion, and
        characterizing the second circulating blood volume by comparing, by the computing device, the at least one second derived parameter to a second baseline value; and
    comparing, by the computing device, the characterization of the first circulating blood volume to the characterization of the second circulating blood volume to characterize the circulating blood volume as a response to the at least one stress.

13. The method of claim 12, wherein the animal is a human.

14. The method of claim 12, wherein applying at least one stress comprises reducing the animal's circulatory volume during dialysis.

15. The method of claim 12, wherein applying at least one stress comprises reducing a blood volume of the animal.

* * * * *